US006222364B1

(12) United States Patent
Smith et al.

(10) Patent No.: US 6,222,364 B1
(45) Date of Patent: Apr. 24, 2001

(54) METHOD OF NUCLEAR QUADRUPOLE RESONANCE TESTING AND METHOD OF CONFIGURING APPARATUS FOR NUCLEAR QUADRUPOLE RESONANCE TESTING

(75) Inventors: John Alec Sydney Smith, London; Martin Blanz, Culham; Michael David Rowe, London, all of (GB)

(73) Assignee: BTG International Limited, London (GB)

( * ) Notice: Subject to any disclaimer, the term of this patent is extended or adjusted under 35 U.S.C. 154(b) by 0 days.

(21) Appl. No.: 09/477,598

(22) Filed: Jan. 4, 2000

Related U.S. Application Data

(62) Division of application No. 08/788,250, filed on Jan. 27, 1997, now Pat. No. 6,091,240.

(30) Foreign Application Priority Data

Sep. 29, 1994 (GB) .................................... 9419695
Feb. 24, 1995 (GB) .................................... 9503806
Sep. 29, 1995 (WO) .................................. PCT/GB95/02318

(51) Int. Cl.[7] ...................................................... G01V 3/00
(52) U.S. Cl. ............................................. 324/300; 324/315
(58) Field of Search .................................. 324/300, 307, 324/309, 310, 314, 315

(56) References Cited

U.S. PATENT DOCUMENTS 3,768,003  10/1973  Amen .................................. 324/300
3,968,424  7/1976  Ernst .................................... 324/300

(List continued on next page.)

FOREIGN PATENT DOCUMENTS 209374  1/1987  (EP) .
242911  10/1987  (EP) .

(List continued on next page.)

OTHER PUBLICATIONS

Rosen, "Selective Detection in NMR by Time–Domain in Digital Filtering" Magnetic Resonance Series, A 107 (1994) pp. 119–125.
Longman, "Zero Filling", A Handbook of Nuclear magnetic Resonance (1987).
Guan, "Generation of optimal excitation pulses for two energy level systems usin an inverse Fourier transform method", The Journal of Chemical Physics, vol. 96, No. 11, (Jun. 1992) pp. 7959–7964.
Goleman, et al., "Multiband Adiabatic Inversion Pulses", Journal of Magnetic Resonance, vol. 101A, No. 2 (Feb. 1993) pp. 136–146.
Ngo, et al., "General Solution to the NMR Excitation Problem for Noninteracting Spins", Magnetic Resonance in Medicine, (May 1987) pp. 217237.

(List continued on next page.)

*Primary Examiner*—Louis Arana
(74) *Attorney, Agent, or Firm*—Pillsbury Winthrop LLP

(57) ABSTRACT

A method of Nuclear Quadrupole Resonance testing a sample containing a given species of quadrupolar nucleus, the sample being subjected to an inhomogeneous distribution of an extrinsic parameter having a variation over the sample over a particular range, comprises applying excitation to the sample at a plurality of different excitation frequencies to excite nuclear quadrupole resonance, such frequencies falling within the resonance frequency range for the nucleus corresponding to the range of the extrinsic parameter, and detecting the resonance response signal.

38 Claims, 14 Drawing Sheets

U.S. PATENT DOCUMENTS

| | | | |
|---|---|---|---|
| 4,034,191 | 7/1977 | Tomlinson et al. | 324/300 |
| 4,703,267 | 10/1987 | Maudsley | 324/307 |
| 4,766,380 | 8/1988 | Den Boef et al. | 324/309 |
| 4,906,932 | 3/1990 | Ordidge | 324/309 |
| 5,153,515 | 10/1992 | Leigh et al. | 324/307 |
| 5,365,171 | 11/1994 | Buess et al. | 324/307 |
| 5,500,591 | 3/1996 | Smith et al. | 324/307 |
| 5,583,437 | 12/1996 | Smith et al. | 324/307 |
| 5,814,987 | 9/1998 | Smith et al. | 324/300 |
| 5,814,989 | 9/1998 | Smith et al. | 324/300 |
| 6,091,240 * | 7/2000 | Smith et al. | 324/300 |

FOREIGN PATENT DOCUMENTS

| | | |
|---|---|---|
| 394504 | 10/1990 | (EP) . |
| 601229 | 6/1994 | (EP) . |
| 1357686 | 6/1974 | (GB) . |
| 1448939 | 9/1976 | (GB) . |
| 2206970 | 1/1989 | (GB) . |
| 2208442 | 3/1989 | (GB) . |
| 2246636 | 2/1992 | (GB) . |
| 2254923 | 10/1992 | (GB) . |
| 2255414 | 11/1992 | (GB) . |
| 2255830 | 11/1992 | (GB) . |
| 2286248 | 8/1995 | (GB) . |
| 91/15754 | 10/1991 | (WO) . |
| 92/17793 | 10/1992 | (WO) . |
| 92/17794 | 10/1992 | (WO) . |
| 92/21987 | 12/1992 | (WO) . |
| 92/21989 | 12/1992 | (WO) . |
| 94/12891 | 6/1994 | (WO) . |
| 95/09368 | 4/1995 | (WO) . |
| 95/16926 | 6/1995 | (WO) . |

OTHER PUBLICATIONS

Guan, "General phase modulation method for stored waveform inverse Fourier transform excitation of Fourier transform ion cyclotron resonance mass spectrometry", Journal of Chem. Phys., vol. 91, No. 2 (Jul. 1989) pp. 775–779.

Tzannes, "Communication and Radar Systems", (1985).

Wittebort, et al., "High–Speed Phase and Amplitude Modulator", Journal of Magnetic Resonance, vol. 96, (1992) pp. 624–630.

Karpowicz et al., "Librational Motion of Hexahydro–1,3, 5–trinitro–s–triazine based on the Temperature Dependence of the Nitrogen–14 Nuclear Quadrupole Resonance Spectra: The Relationship to Condensed–Phase Thermal Decomposition", Jounral of Phys. Chem. vol. 87, No. 12 (1983) pp. 2109–2112.

Marshall, et al., "Fourier Transforms in NMR, Optical, and Mass Spectrometry", (1990) pp. 107–109.

* cited by examiner

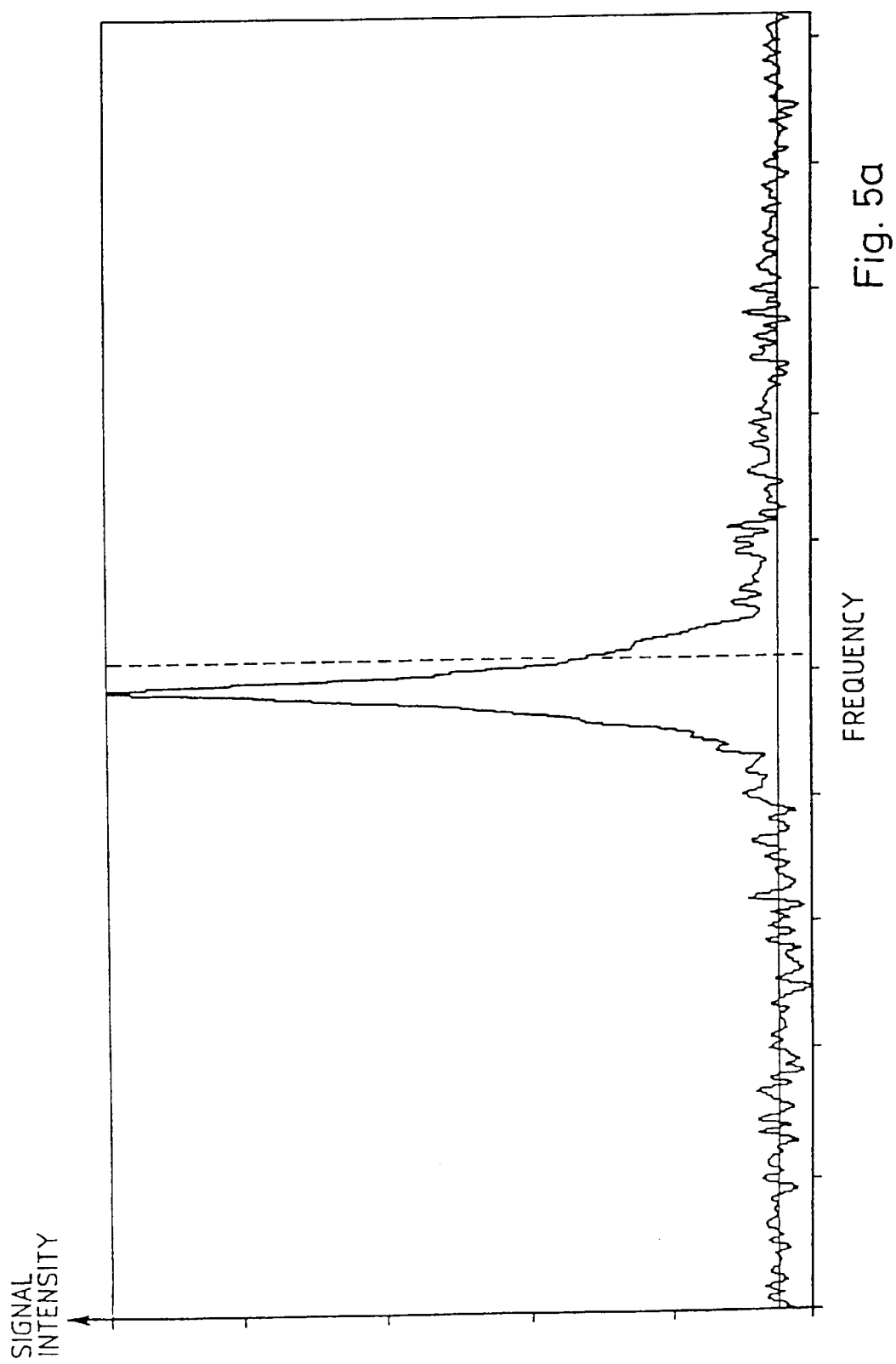

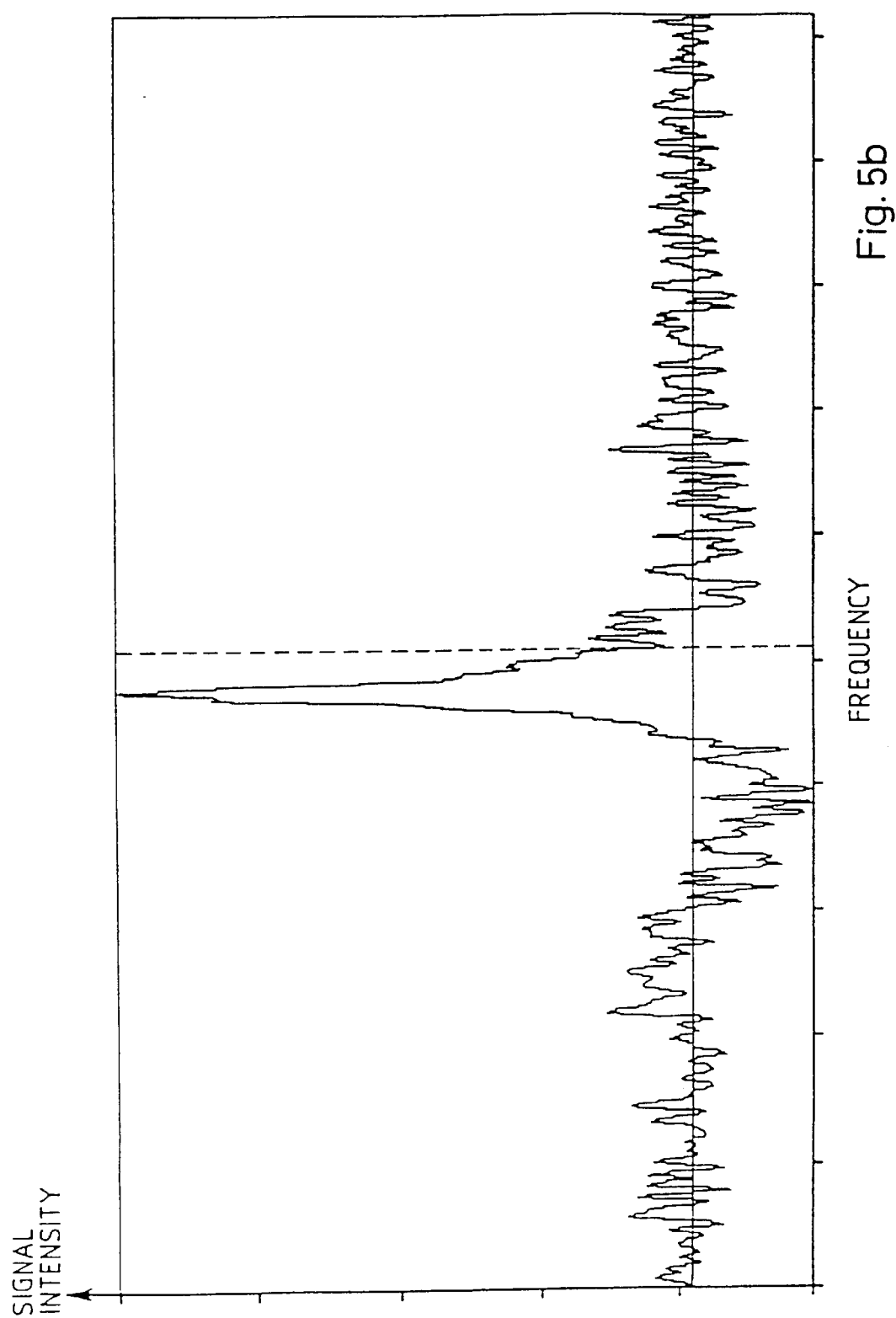

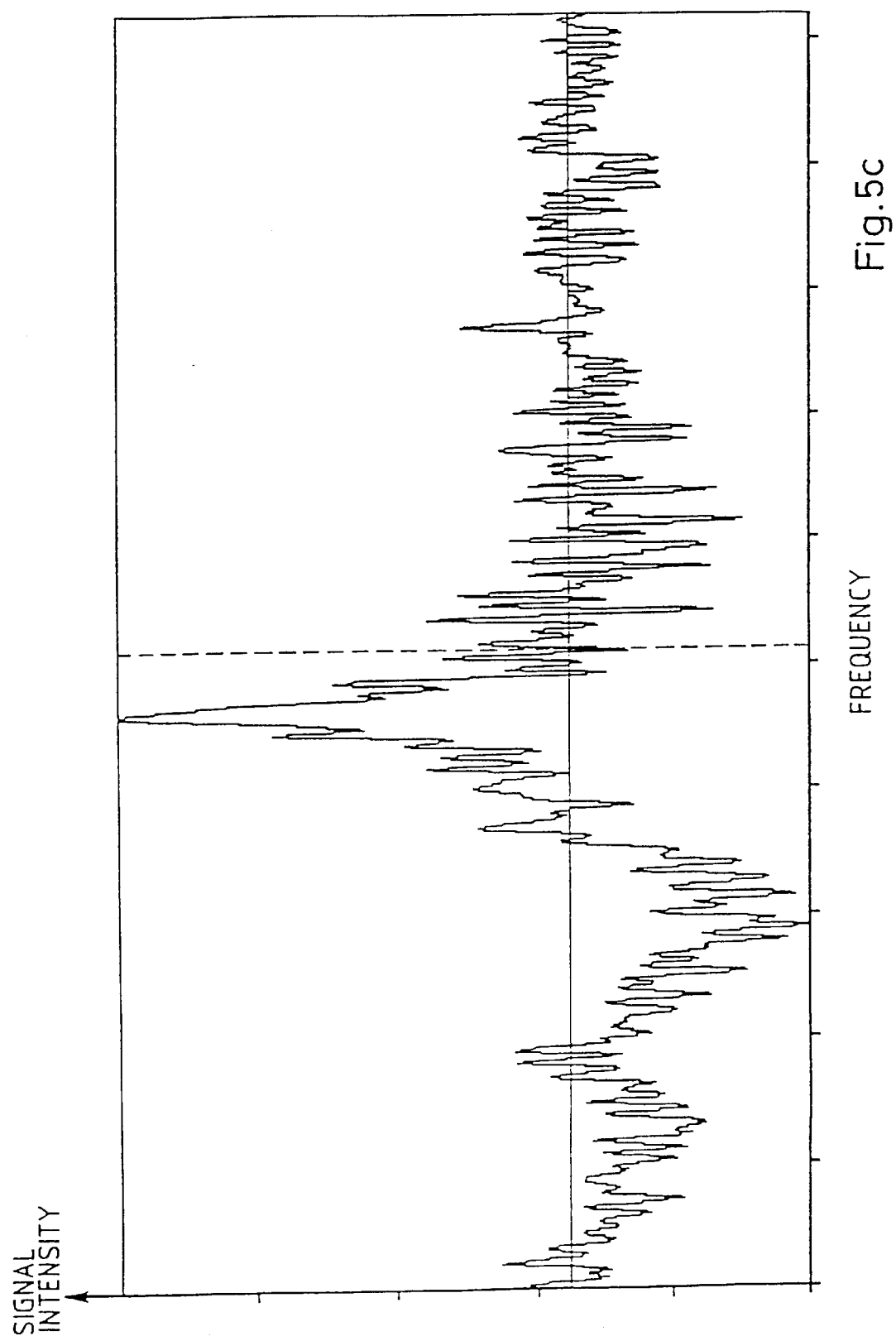

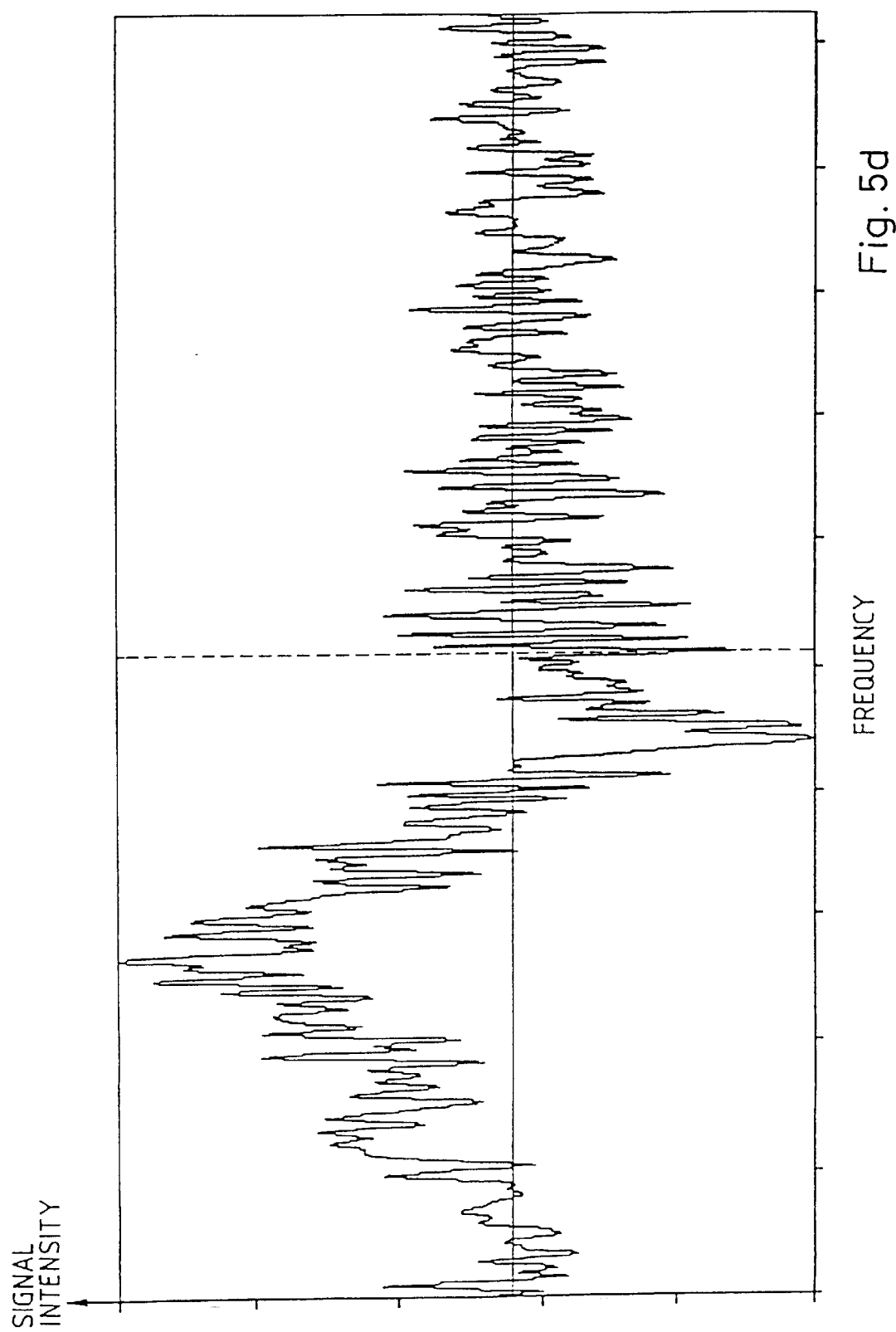

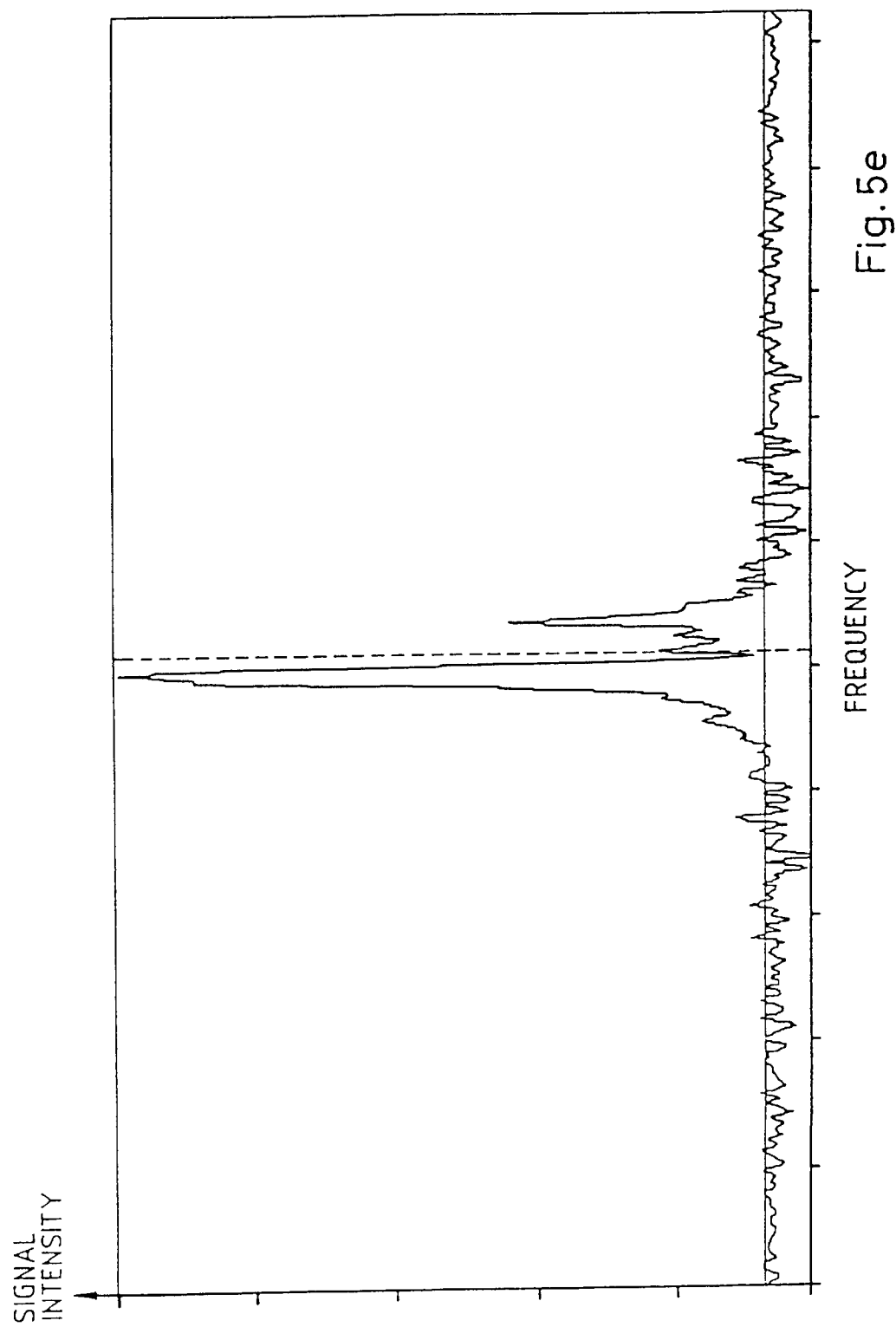

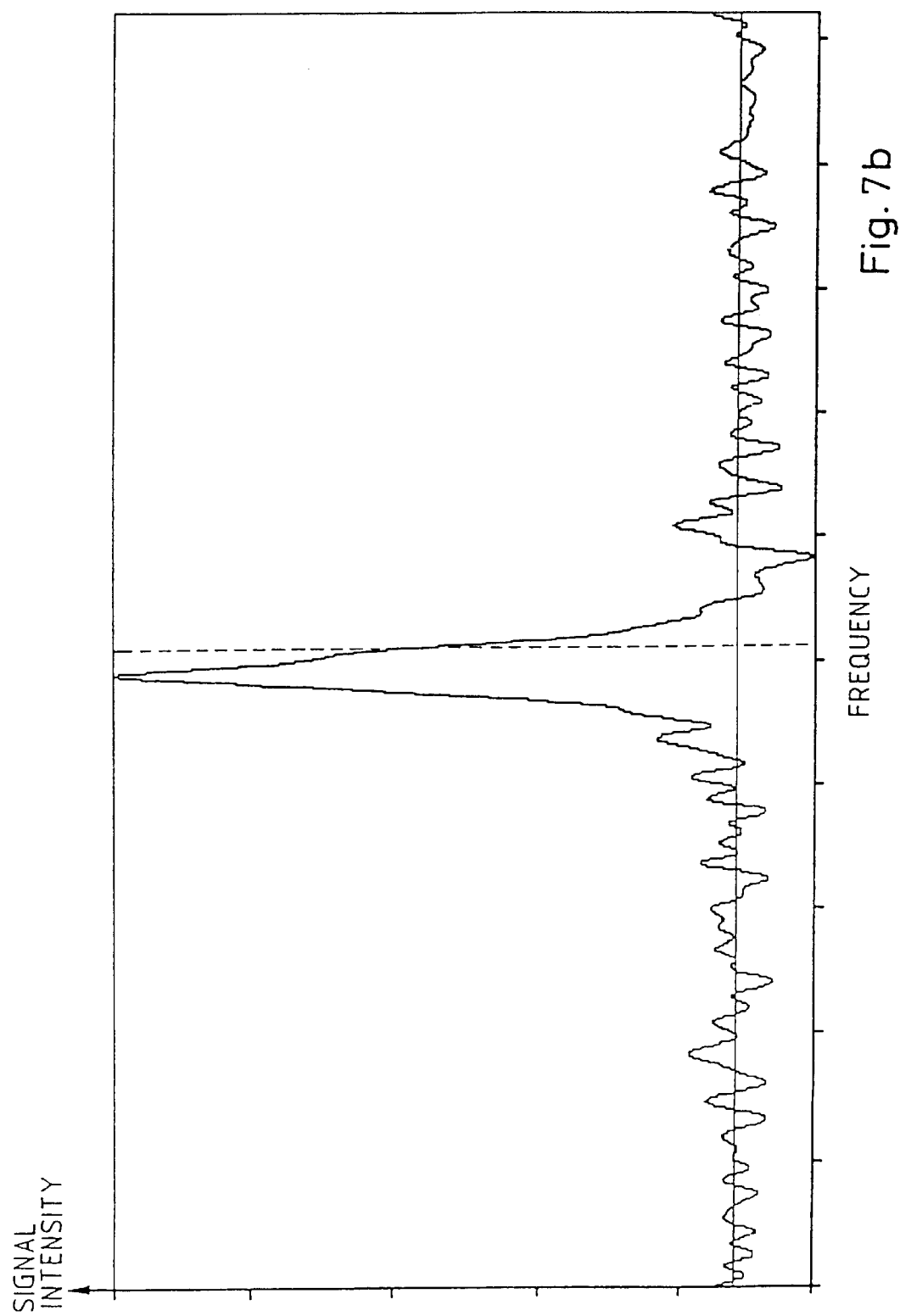

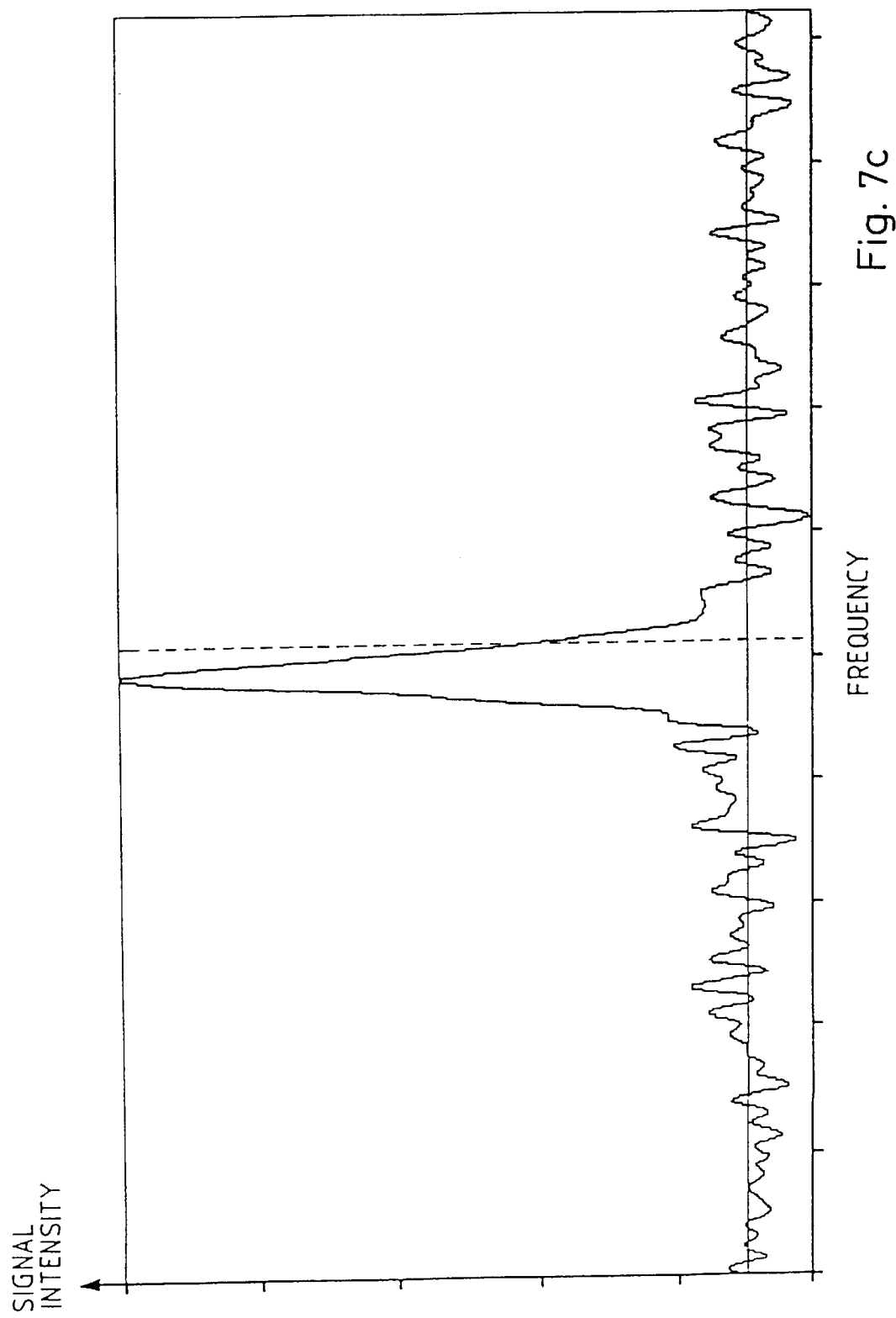

METHOD OF NUCLEAR QUADRUPOLE RESONANCE TESTING AND METHOD OF CONFIGURING APPARATUS FOR NUCLEAR QUADRUPOLE RESONANCE TESTING

This application is a divisional of Ser. No. 08/788,250 filed Jan. 27, 1997 now U.S. Pat. No. 6,091,240.

The present invention relates to a method of Nuclear Quadrupole Resonance (NQR) testing a sample, and to a method of configuring apparatus for NQR testing such a sample. It relates more particularly to the detection of the presence of a particular substance, such as explosives or narcotics, containing a given species of quadrupolar nucleus.

As an example, the invention has application to the detection in the field of $^{14}N$ quadrupole resonance signals from the explosive RDX concealed in parcels or luggage or on the person, or deployed in explosive devices. As another example, it has application to the detection of concealed drugs, for instance at airports. Typical explosives might be RDX, HMX, PETN and TNT, whilst typical drugs might be cocaine or heroin.

NQR measurements have the advantage that they do not require the sample to be placed in a strong magnetic field, and therefore do not require the large, expensive and sample-size limiting magnet structures which are needed for nuclear magnetic resonance (NMR) measurements.

Quadrupolar nuclei have a nuclear spin quantum number I equal to or greater than unity ($I \geq 1$). If they are half integral, the quadrupole interaction (in zero magnetic field) produces two doubly degenerate levels for the case of $I=\frac{3}{2}$ and one allowed transition ($\frac{1}{2} \rightarrow \frac{3}{2}$), three doubly degenerate levels for $I=\frac{5}{2}$ and two strongly-allowed ($\frac{1}{2} \rightarrow \frac{3}{2}$, $\frac{3}{2} \rightarrow \frac{5}{2}$) and one weakly-allowed ($\frac{1}{2} \rightarrow \frac{5}{2}$) transition, and so on. For integral spin nuclei, the most important of which is $^{14}N$ with $I=1$, there are usually three levels and three transition frequencies, dropping to one for nuclei in axially-symmetric environments. All these transitions have one or more characteristic frequency which can be used to identify the substance under investigation. These frequencies do not depend on the presence of other substances, provided that they do not have transitions in the same frequency range.

Nuclear quadrupole resonance response signals are conventionally detected by means of pulsed radiofrequency (rf) radiation of the correct excitation frequency ($v_o$) to excite the selected transition (at a resonance frequency $v_Q$); a pulse of preset width t, rf field amplitude $B_1$, and flip angle generates a decaying signal immediately following the pulse known as a free induction decay (f.i.d.).

Apparatus capable of detecting NQR response signals is disclosed in International Patent Publication No. WO 92/17794, in the name of British Technology Group Limited, whose disclosure is incorporated herein by reference.

It was reported in that document that environmental variations (particularly temperature variations) between one location and another can influence properties such as the resonance frequency of the particular NQR substance of relevance and affect the test results. Techniques for coping with such influences are disclosed in the same document.

Problems have now been encountered which are associated with temperature inhomogeneities actually within the sample. In circumstances where a sample is subjected to even modest variations in temperature over the sample (say, a variation of 1 or 2° C. over the length of an elongate sample), the temperature inhomogeneity may be such that signals from the sample can only be detected with difficulty (or not at all) by normal means. It is to be noted that substances of interest, such as the explosive RDX, can have relatively low thermal conductivities, so that sustained temperature inhomogeneities can be commonly encountered.

The present invention seeks to overcome these and other problems.

According to the present invention, there is provided a method of Nuclear Quadrupole Resonance testing a sample containing a given species of quadrupolar nucleus, the sample being subjected to an inhomogeneous distribution of an extrinsic parameter, the parameter having a variation over the sample over a particular range, the method comprising:

applying excitation to the sample at a plurality of different excitation frequencies to excite nuclear quadrupole resonance, such frequencies falling within the resonance frequency range for the nucleus corresponding to the range of the extrinsic parameter; and detecting the resonance response signal.

In a closely related aspect, the invention provides a method of configuring apparatus for Nuclear Quadrupole Resonance testing a sample, containing a given species of quadrupolar nucleus, which can be subjected to an inhomogeneous distribution of an extrinsic parameter, the apparatus, including means for applying excitation to the sample to excite nuclear quadrupole resonance, the method comprising:

selecting a range of the extrinsic parameter over which it is expected that the parameter will vary over the sample;

determining a resonance frequency range for the nucleus corresponding to the selected range; and arranging the excitation means to apply excitation at a plurality of different excitation frequencies, such frequencies falling within the determined resonance frequency range.

By arranging for the excitation to be applied at a plurality of excitation frequencies falling within the resonance frequency range of interest, the sensitivity of the tests can be improved.

The present invention arises from the discovery, made pursuant to the present invention, that the problems encountered with the prior art technique arise in part from a dephasing of the NQR resonance response signal due to the inhomogeneous distribution of the extrinsic parameter. For instance, if the extrinsic parameter is temperature, relatively small inhomogeneities in temperature within the sample can give rise to a significant variation of the resonance frequency of the quadrupolar nucleus. It is this variation which can in turn give rise to the dephasing of the signal.

The use of plural excitation frequencies serves to divide the sample notionally into at least two temperature zones corresponding to the respective frequency ranges covered by the different excitation frequencies. Thus, by effectively dividing up the total frequency range into smaller portions, the dephasing effects can be lessened.

For the purposes of the present invention, the relevant resonance response signal would usually be the free induction decay (f.i.d.).

As used herein, the term "excitation frequency" in the context of pulsed excitation preferably connotes the central "carrier" frequency of the relevant excitation pulse where the context so demands.

In putting the aforementioned configuration method aspect of the invention into practice, the apparatus may be configured by, say, appropriate design of or adjustments to its controlling hardware (or software). Such configuration may take place at the factory before delivery of the apparatus.

Preferably, the excitation comprises pulses at the different excitation frequencies which are arranged to have respective excitation frequency ranges which are substantially non-overlapping. By providing substantially non-overlapping frequency ranges, dephasing effects can be reduced.

For the same reason, preferably the excitation comprises pulses at the different excitation frequencies, the pulses being shaped so as to have a substantially rectangular frequency profile. By way of contrast, conventional simple "rectangular" pulses have a profile in the frequency domain which actually possesses substantial frequency sidebands, often known as "Gibbs oscillations". Such pulses are only "rectangular" in the time domain. If such pulses were employed, either—if the pulses were substantially overlapping—very substantial dephasing effects could be caused, particularly by the sidebands, or—if there were no overlap—a substantial proportion of the potential signal could be lost. Pulse shaping as described above can make optimal use of the time available for the test.

The pulses are preferably frequency/phase swept. This can permit pulse length to be kept at a low value.

From the point of view of reducing the dephasing problem, the separation between the excitation frequencies should be as small as possible, although clearly there are practical limits. Hence, preferably the frequency separation between adjacent excitation frequencies is less than 0.1% of one such excitation frequency, preferably less than 0.06%, 0.04%, 0.02%, 0.01% or 0.005% of one such excitation frequency. Preferably also the frequency separation between adjacent excitation frequencies is less than 5 kHz, preferably less than 3, 2, 1, 0.5 or 0.25 kHz.

Again, from the point of view of reducing the dephasing problem, as many excitation frequencies as possible should be employed, although clearly again there are practical limits to how many such frequencies can be employed. Hence, preferably the number of such different excitation frequencies is greater than 2, preferably greater than or equal to 4, 8, 16 or 32. Multiples of 2 frequencies may be preferable from a practical point of view for ease of programming the NQR testing apparatus.

Preferably, the excitation at adjacent excitation frequencies is applied or arranged to be applied at different times. By this feature, dephasing effects between the various resonance response signals can be reduced, especially if the time of application of the excitation at the adjacent frequencies is such that detection of the signal from one frequency is substantially completed and/or the f.i.d. has substantially decayed to zero before detection of the signal from the other is started.

Preferably, the respective resonance response signal corresponding to each excitation frequency is detected or arranged to be detected at that excitation frequency. This is an important feature, without which many of the advantages of the invention could be foregone because of dephasing effects in the detection circuitry itself.

Preferably, at least part of the resonance response signal is detected or arranged to be detected before the signal has dephased to an undetectable level due to the inhomogeneous distribution of the extrinsic parameter. This feature is based on the discovery discussed previously concerning the presence of dephasing effects when the sample is subjected to an inhomogeneous distribution of the extrinsic parameter.

The feature is also provided independently. Hence, according to the present invention, there is provided a method of Nuclear Quadrupole Resonance testing a sample, the sample being subjected to an inhomogeneous distribution of an extrinsic parameter, the method comprising:

applying excitation to the sample to excite nuclear quadrupole resonance; and detecting at least part of the resonance response signal before the signal has dephased to an undetectable level due to the inhomogeneous distribution of the extrinsic parameter.

By "undetectable" may in particular be meant that the response signal is of the order of or less than the root mean square noise (which is typically one fifth of the peak to peak noise excursion), although this definition is not intended to be exclusive.

The invention also provides in a closely related aspect a method of configuring apparatus for Nuclear Quadrupole Resonance testing a sample which can be subjected to an inhomogeneous distribution of an extrinsic parameter, the apparatus including means for applying excitation to the sample to excite nuclear quadrupole resonance and means for detecting the resonance response signal, the method comprising:

selecting a range of the extrinsic parameter over which it is expected that the parameter will vary over the sample;

determining the time taken for the resonance response signal to dephase to a selected extent due to the inhomogeneous distribution of the extrinsic parameter and given the selected range of the extrinsic parameter; and arranging the detection means to detect at least part of the resonance response signal before the signal has dephased to the selected extent.

The selected extent of the dephasing may be to a level where the response signal is undetectable, or may be to some higher level, such as less than 50%, preferably less than 20 or 10% of the peak response signal.

Preferably, the excitation is or is arranged to be pulsed excitation, and, for the or each pulse, at least part of the resonance response signal is or is arranged to be detected before the expiry of a time period, starting with the beginning of that pulse, equal to the reciprocal of once, preferably two, five or ten times the beat frequency corresponding to the two resonance frequencies corresponding to the two limits of the range of the extrinsic parameter to which the sample is subjected or is expected to be subjected. This feature provides specific time limits before which at least part of the detection of the response signal should preferably be completed before the signal dephases.

In order to determine the beat frequency corresponding to the two limits of the range of the extrinsic parameter to which the sample is subjected or expected to be subjected, first the resonance frequencies corresponding to these two (upper and lower) limits may be determined; the beat frequency is then the difference between these two resonance frequencies. The reciprocal of the beat frequency provides a measure of the duration of the dephasing of the response signal due to the aforementioned inhomogeneities to which the sample is subjected.

Dephasing of the response signals does not only occur once the pulse has terminated; except in the case of a pulse of negligible duration, dephasing occurs to an extent even before termination. This is especially true where shaped pulses are being employed. Such pulses may be of relatively long duration, and, covering as they usually do a relatively broad frequency bandwidth, may excite particular frequencies of interest early during the pulse. From such a point onwards deleterious dephasing effects may occur. Hence it is important to control carefully the length of the excitation pulses.

Therefore, if the excitation is or is arranged to be pulsed excitation, preferably the duration of the or each pulse is or is arranged to be less than twice the free induction decay time, $T_2^*$, appropriate to the NQR resonance, and more preferably the duration is or is arranged to be less than 100%, 75%, 50% or even 25% of $T_2^*$. This is an important feature, which can ensure that unacceptable loss of the NQR response signal due to the aforementioned inhomogeneities does not arise before the signal is detected.

For the same reason, the duration of the or each pulse is or is arranged to be preferably less than 5 ms, more preferably less than 3 ms, 2 ms, 1 ms, 0.7 ms, 0.4 ms or 0.1 ms. It is especially important to maintain such durations if the pulses are shaped pulses, since in these circumstances in general terms longer pulses are more likely to be used.

The aforementioned durations are of particular relevance to the explosive RDX, which has a value of $T_2^*$ at 298 K (room temperature) of roughly 1.4 ms for the 5.19 MHz line.

The extrinsic parameter may be temperature, pressure, force (such as bending stress applied to the sample) or a magnetic field; in other words the extrinsic parameter may be any influence applied, whether directly or indirectly, externally to the material of the sample. This is distinct from internal, intrinsic properties of the sample, such as electric field gradient inhomogeneities due to sample defects.

In general terms, the range or expected range of the extrinsic parameter may be less than 100%, preferably less than 10 or 1%, of its mean absolute value. Similarly, the range may be greater than 0.01%, preferably greater than 0.1 or 1%, of the mean value.

More specifically, if the extrinsic is temperature, then preferably the range or expected range of temperature is less than 10° C., preferably less than 6° C., 4° C., 2° C., 1° C. or 0.5° C., although in reality, of course, the range may be greater than any of these values.

Another preferred feature of the invention is that the nuclear quadrupole resonance of the sample having the least temperature sensitivity is excited or arranged to be excited. This is an important feature, which may be provided independently. It may be used in combination with any of the aforementioned features.

Hence, according to a further aspect of the present invention, linked to the previous aspects by the unifying concept of maintenance of sensitivity in the present of an inhomogeneous distribution of an extrinsic parameter, there is provided a method of Nuclear Quadrupole Resonance testing a sample containing a given species of quadrupolar nucleus, comprising applying excitation to the sample to excite that quadrupole resonance of the given nuclear species for which a particular property has the least sensitivity to a given extrinsic parameter, and detecting the resonance response signal.

If, for example, the resonance having the least temperature sensitivity is employed, then there are less likely to be temperature inhomogeneity induced dephasing problems.

To avoid dephasing problems, preferably the particular property is resonance frequency. Alternatively or additionally, it may be some other property such as spin-lattice relaxation time, $T_1$, or spin-spin relaxation time, $T_2^*$. Preferably more than one such property exhibits the least sensitivity to the given extrinsic parameter.

Either the sample may be subjected to an inhomogeneous distribution of an extrinsic parameter, or the value of the extrinsic parameter may be unknown.

Usually the sample would comprise a substance having two, three or more distinct resonance frequencies. If the sample does comprise a substance which has a plurality of distinct resonance frequencies or sets of resonance frequencies, the resonance which is excited or arranged to be excited may not have the highest resonance frequency or may not have a resonance frequency in the highest set of resonance frequencies. Put simply, the resonance which is excited or arranged to be excited may not have the highest frequency of the resonance frequencies.

In the preferred embodiment, the sample comprises the explosive RDX, and preferably the resonance at either 5.05 MHz, or 5.19 MHz, or 5.24 MHz or 3.41 MHz, at 298 K, is excited or arranged to be excited.

The last such resonance, at 3.41 MHz at 298 K, may be particularly useful, since it has been discovered pursuant to the present invention that this resonance is unusually temperature insensitive, and hence is less likely to be associated with temperature inhomogeneity induced dephasing problems. Since this resonance frequency is not the highest such frequency for RDX, and since further it has a relatively low value of $T_2^*$, use of this particular resonance would be expected to lead to a sharp loss in sensitivity by comparison with use of one of the higher frequencies. For this reason, it is believed that use of this resonance has not previously been contemplated. However, as explained later, if the appropriate excitation pulse sequence is employed, it has now been found that the loss in sensitivity may in fact only be marginal, and may be outweighed by the advantages of employing this particular resonance.

The second of the four resonances mentioned above (5.19 MHz) has a somewhat smaller dependence on temperature than the first or third such resonance, and so is also preferred.

Preferably, the excitation is arranged to generate an echo response signal. In the context of temperature inhomogeneities or similar effects to which the sample may be subjected, this is a particularly important feature, since the use of echoes can to an extent re-focus signals which may have begun to de-phase due to these inhomogeneities. This is another important feature, which may be provided independently. It may be used in combination with any of the aforementioned features.

Hence, according to a further aspect of the present invention, linked to the previous aspects by the unifying concept of maintenance of sensitivity in the presence of an inhomogeneous distribution of an extrinsic parameter, there is provided a method of Nuclear Quadrupole Resonance testing a sample containing a given species of quadrupolar nucleus, the sample being subjected to an inhomogeneous distribution of an extrinsic parameter, the method comprising:

applying excitation to the sample to excite nuclear quadrupole resonance, the excitation being arranged to generate an echo response signal; and detecting the response signal.

As mentioned previously, a particularly preferred feature is the use of so-called "shaped pulses", as described in International Patent Publication No. WO 95/09368, whose disclosure is incorporated herein by reference. In broad terms, a shaped pulse may be thought of as one for which the time domain waveform of the excitation is either phase modulated or amplitude modulated, or both phase modulated and amplitude modulated.

In the preferred embodiment, specific types of shaped pulses are employed. For example, if the excitation is pulsed excitation covering a given frequency range, preferably the excitation is applied or arranged to be applied to the sample in such a way that the phase of the excitation varies generally non-linearly with the excitation frequency over the given range.

Yet again, more preferably the phase of the excitation varies or is arranged to vary generally quadratically with the frequency off-set.

A selected NQR resonance may be excited, and, if so, the duration of the excitation is preferably less than twice the free induction decay time, $T_2^*$, appropriate to that resonance. This is an important feature, which can ensure that unacceptable loss of the NQR response signal does not arise before the signal is detected. The duration is in fact preferably less than 100%, 75% or even 50% of $T_2^*$.

Further preferred features are described in International Patent Publication No. WO95/09368.

The theory underlying the present invention, as well as preferred features of the present invention, are now described, by way of example only, with reference to the accompanying drawings, in which:

FIGS. 5 show spectra obtained at five different times during a first experiment;

Figure 1:
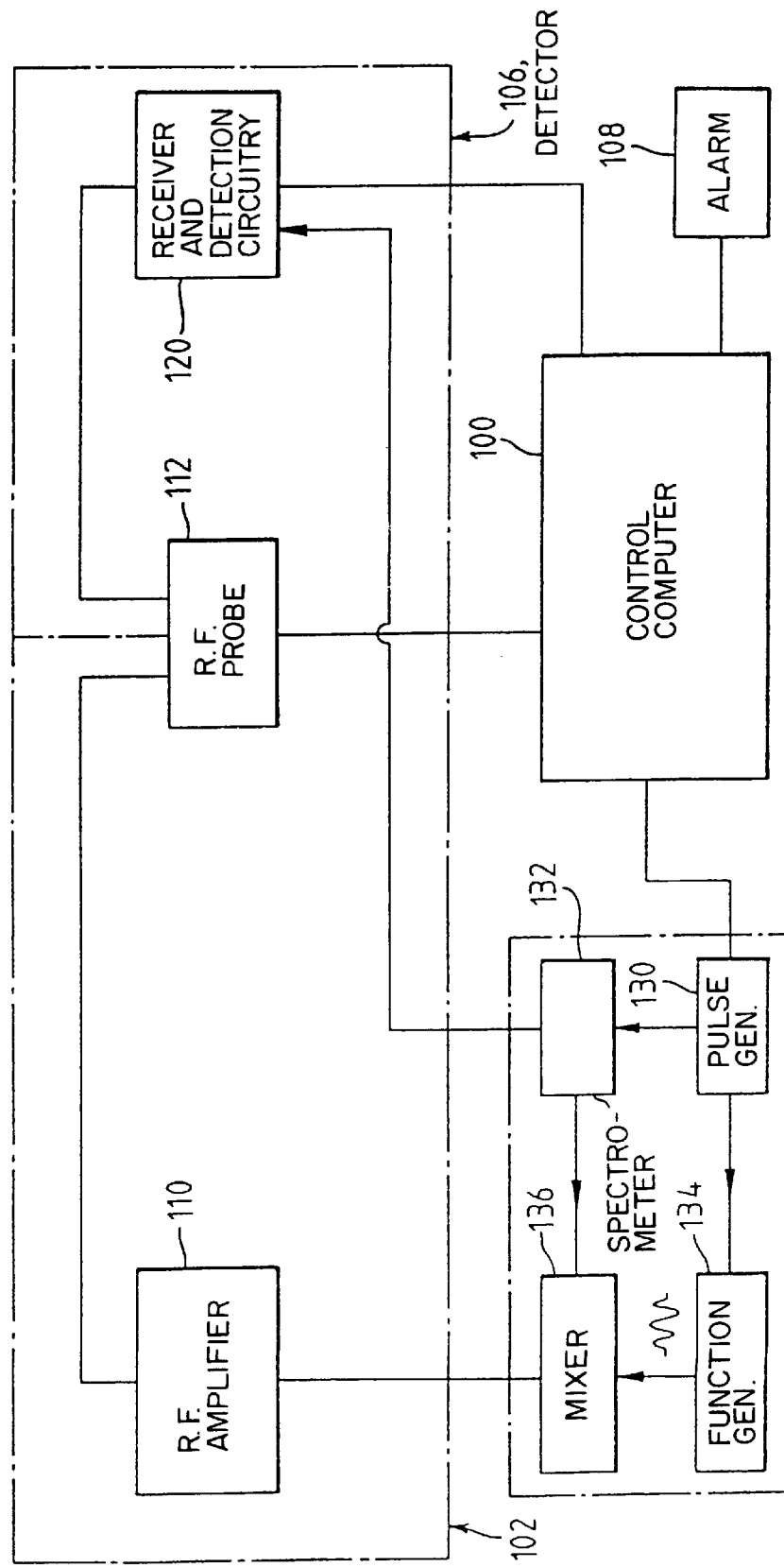
FIG. 1 is a block diagram of a preferred embodiment of NQR testing apparatus according to the present invention.

The theory underlying the present invention is first described in detail. In particular, the following text demonstrates how the dephasing effects referred to previously can arise, and discusses the likely extent of such effects.

For simplicity, at first a sample is assumed having two distinct temperature regions, region A at a temperature of $T_A$, and region B at a slightly different temperature $T_B$. The small difference $(T_A - T_B)$ is defined as $\Delta T$, and is equal in the present example to 1° C. The sample contains or consists of the explosive RDX. The two regions A and B are assumed to contain equal amounts of the explosive.

The three sets of NQR resonance frequencies for RDX, $v_x$, $v_y$, $v_z$, are all triplets due to crystal effects; near 298 K, the highest set ($v_x$) occurs at 5047 ($N_1$), 5192 ($N_2$), and 5240 (N3) kHz. Between 240 and 340 K, their frequencies in kHz follow closely the equations $$N_1 \, v_Q^{(1)} = 5210 - 0.548T$$

$$N_2 \, v_Q^{(2)} = 5345 - 0.517T$$

$$N_3 \, v_Q^{(3)} = 5414 - 0.584T \quad (1)$$

where T is temperature.

For a small variation in temperature, $\Delta T$, $v_Q^{(2)}$ will shift from $$5345 - 0.517 \, T \quad (2)$$

to $$5345 - 0.517 = (T + \Delta T) \quad (3)$$

Subtracting (3) from (2), the shift in resonance frequency, $\Delta v_Q^{(2)}$, corresponding to a $\Delta T$ variation in temperature, is equal to $$-0.517 \Delta T$$

Hence for the aforementioned $N_2$ resonance of RDX, response signals which emanated simultaneously from regions A and B of the sample would interfere one with another, the beat frequency of the interference being equal to $0.517 \Delta T$ kHz=517 Hz, based on $\Delta T=1°$ C. One cycle of the beat frequency therefore has a duration of approximately 2 ms. The resonance response signal from the sample would decay to zero in one quarter of the cycle, that is, in a little over 0.5 ms in the present simple example.

In terms of commonly used sequences of excitation pulses, a duration of 0.5 ms is not especially long, and, of course, if $\Delta T$ were 3° C. instead of 1° C., the duration would only be roughly 0.17 ms, which is of the same order of magnitude as the dead time due to the receiver coil ring down following the application of an excitation pulse may commonly be. In addition, if shaped excitation pulses are employed, these may typically themselves have a duration of up to 0.5 ms or greater, and the particular frequency of interest may be excited relatively early in the pulse. Hence, in such circumstances, in the absence of the techniques of the present invention, it is possible that the response signals may have dephased due to the temperature inhomogeneity even before the receiver dead time has finished, and that, in this worst case, no response signal at all may be detected.

Of course, the simple example provided above is not entirely realistic. In fact, the variation of temperature over the sample is likely to be highly non-linear, with, say, hot spots where a portion of the sample has been exposed to some source of heat such as sunlight, but the remainder of the sample being at a relatively constant temperature. The above example serves to provide a conservative indication of the likely effects of temperature inhomogeneities. Worse cases can be envisaged, but such cases are less likely to occur in practice.

Inhomogeneities induced by extrinsic parameters other than temperature are likely to be less severe in general terms, although certain inhomogeneities, such as might be caused by a specific stress to which the sample is subjected (such as a bending moment), might give rise to particular problems.

It is to be noted from Equations (1) above that the $N_2$ resonance has a lower temperature dependence than the $N_1$ or $N_3$ resonances, and may therefore give rise to fewer dephasing problems.

A preferred embodiment of apparatus for putting the present invention into effect is now described with reference to FIG. 1. This apparatus is substantially the same as that described in International Patent Publication No. WO 95/09368, to which reference should also be made for further details and information.

A preferred embodiment of NQR testing apparatus is now described with reference to FIG. 1. This embodiment is particularly suited to the detection of the presence of a particular substance in a sample (such as a suitcase or the like). The apparatus comprises in general terms a control computer 100, means 102 for applying one, or more usually several, continuous radio-frequency excitation pulses to the sample covering a selected excitation frequency range and for a given duration, means 104 for generating shaped pulses for passing to the applying means 102, means 106 for detecting the NQR response signal, and means 108 for producing an alarm signal in dependence upon whether a given threshold of detection for the presence of the particular substance has been exceeded. The alarm signal would normally be used to activate an audio or visual alarm 108 to alert the operator to the presence of the substance under test. Although not illustrated, the apparatus would normally include some means, such as a conveyor, for transporting the sample relative to the apparatus, so that a series of samples can be tested "on the fly".

With the technique of the preferred embodiment, each individual excitation pulse is shaped such that phase varies during the pulse, and preferably over a substantial proportion of the duration of the pulse, say, over at least 50%, more preferably at least 75 or 90%, most preferably over the entirety of the pulse. The phase modulation is preferably continuous in time, the excitation pulse itself being continuous in time (that is, there is no period during the pulse when the excitation is off, although the excitation may instantaneously pass through zero).

In more detail concerning the preferred embodiment, the excitation pulse application means 102 includes a radio-frequency power amplifier 110 whose output is connected to an r.f. probe 112 which contains one or more r.f. coils disposed about the sample to be tested (not shown).

The r.f. probe 112 also forms part of the detecting means 106 which also includes r.f. receiver and detection circuitry 120.

The shaped pulse generating means 104 comprises a pulse programmer 130 for producing trigger signals to time the pulse, a spectrometer 132, manufactured by SMIS, United Kingdom, for generating a radio-frequency carrier signal at a known carrier reference frequency and fixed amplitude, the signal being gated by the trigger signals, a function generator 134, manufactured by Farnell, United Kingdom (Model No. SFG 25), for generating from a stored representation a waveform to modulate the amplitude of the carrier signal, the output of the function generator also being initiated by the trigger signals, and a double balanced mixer 136 for mixing the modulating waveform and the carrier signal and passing the mixed signal to the r.f. power amplifier 110. It will thus be appreciated that the shaped pulse generating means 104 is capable of applying to the sample a time-domain excitation waveform which is amplitude but not otherwise phase modulated.

The computer 100 ultimately controls all pulses, their radio-frequency, time, width, amplitude and phase. It is arranged to time the application of the excitation pulses substantially simultaneously with the arrival of a particular sample adjacent the probe 112. It also acts to receive the detected NQR response signal from the detecting means 106 and to process it, carry out signal addition or subtraction, and finally trigger the alarm 108 if appropriate.

The apparatus of FIG. 1 is suitable for generating a purely amplitude modulated time domain excitation waveform. Although the present invention would more normally require the generation of a phase as well as amplitude modulated time domain excitation waveform, there are nonetheless certain cases for which this apparatus can be used. These are described in International Patent Publication No. WO95/09368.

Figure 2:
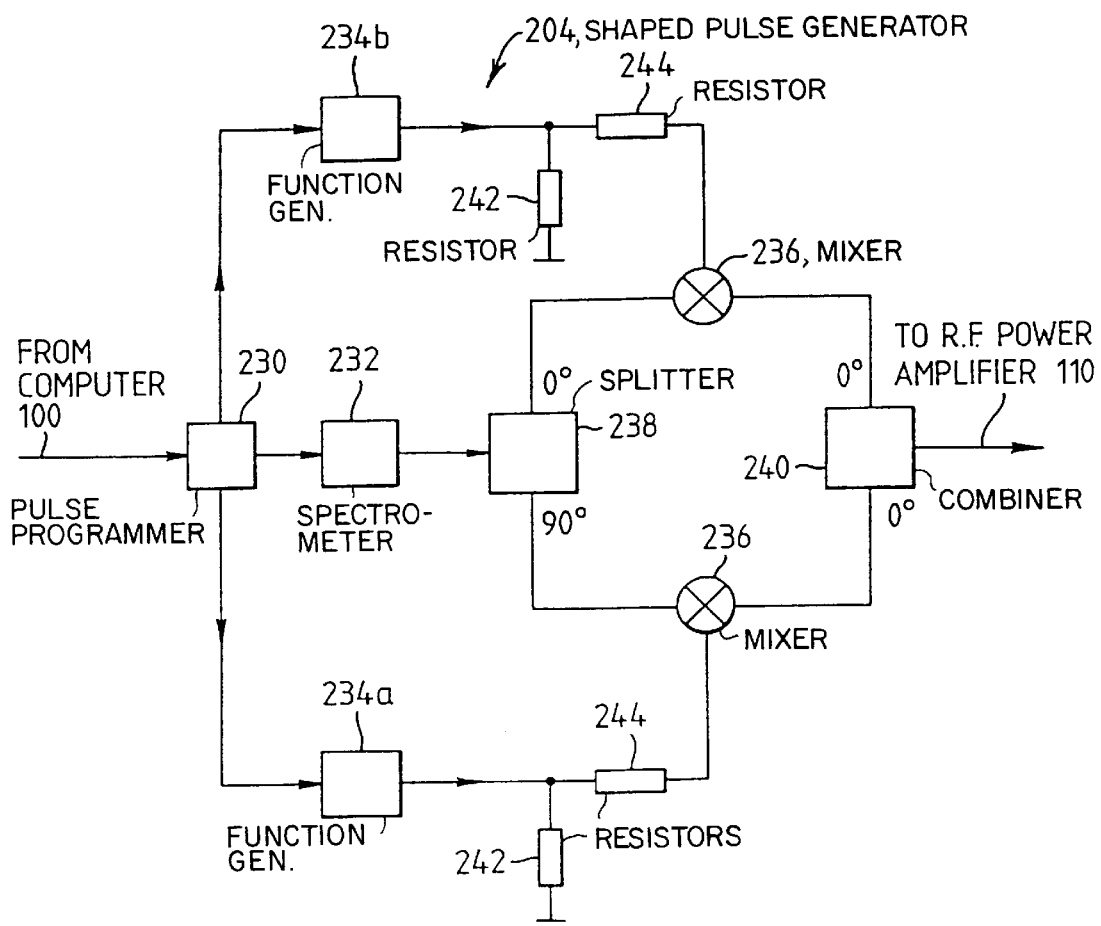
FIG. 2 is a block diagram of a variant of the preferred embodiment of NQR testing apparatus.

A variant of the preferred embodiment of NQR testing apparatus is now described with reference to FIG. 2. Only the shaped pulse generating means 204 is illustrated; the remaining components are identical to those of the embodiment described with reference to FIG. 1. In broad terms, the generating means 204 of the variant is similar to the generating means 104, except that it is a double channel rather than a single channel arrangement. Hence it can produce a waveform which is phase as well as amplitude modulated.

The variant again includes a pulse programmer 230 and spectrometer 232. However, two function generators 234a and 234b, and two double balanced mixers 236 are provided. In addition, a quadrature hybrid 0–90° splitter 238, a combiner 240 and resistors 242 and 244 are provided. In this embodiment, the splitter 238 is a 5 MHz splitter made by Mini Circuits (U.S.A.) and bearing Model Number PSCQ 2-5-1; the combiner 240 and mixers 236 are both made by Hatfield (U.K.) and bear the Model Numbers DP102 and MC 291 respectively. The resistors 242 are 56Ω whilst resistors 244 are 560Ω. The whole network of resistors 242 together with resistors 244 results in a resistance of 50Ω seen by function generators 234.

The variant functions as follows. Spectrometer 232 is gated and the outputs of the function generators 234 are initiated by the pulse programmer 230 as described in relation to the first embodiment. The splitter 238 produces from the radio-frequency carrier signal two radio frequency signals in relative quadrature. The function generators 234a and 234b generate the real and imaginary parts respectively of the modulating waveform. The resistors 242 provide impedance matching with the cables from the function generators, whilst the resistors 244 convert the voltage output of the function generators to a current output for passing to the mixers 236. After mixing of the relevant modulating waveforms and carrier signals in the mixers 236, the two resultant waveforms are combined in the combiner 240 to form an amplitude and phase modulated signal for passing to the radio-frequency power amplifier 110.

In a modification of the variant, a single function generator could be provided. The output of the generator would be passed through a further quadrature hybrid, the two outputs of which would be passed to the respective mixers 236. This modification would produce the type of modulation known in the field of telecommunications as single side-band modulation with suppressed carrier. The modification has the possible disadvantage that the quadrature hybrid would work at very low frequencies.

Examples of the use of this variant of the apparatus are described in International Patent Publication No. WO 95/09368.

Various specific stipulations may need to be adhered to when putting the present invention into effect using the apparatus described above.

Firstly, the apparatus of the preferred embodiment of the invention is operated at a plurality of excitation frequencies. Repeating series of pulses at each frequency are applied in staggered, interleaved fashion so that, if, say, there are only two excitation frequencies, a first pulse at a first frequency is applied, then a first pulse at a second frequency, then a second pulse at the first frequency, a second pulse at the second frequency, and so on. The interval between the pulses at the various frequencies is sufficient to allow the majority, if not all, of the free induction decay signal from one pulse to be detected before the next pulse at the next frequency is applied.

A suitable pulse timing diagram for the preferred embodiment of the present invention is provided in FIG. 3 and described in detail later.

Secondly, in detecting the resonance response signals, it is important that each signal is actually detected at its relevant excitation frequency if some of the advantages of the invention are not to be lost. In conventional NQR tests, the resonance response signal detection means incorporates a phase-sensitive detector which mixes the single excitation frequency, supplied by the spectrometer, with the frequency of the response signal. Response signals which are off-set from the excitation frequency cause beat frequencies in the detection means in proportion to the frequency off-set. With the present invention, significant frequency off-sets due to the temperature inhomogeneity in the sample could give rise to significant dephasing effects in the detection means. Hence it is important that the receiver and detection circuitry denoted as 120 in FIG. 1 detects each response signal at the relevant excitation frequency rather than, say, at a single mean frequency. Thus FIG. 1 shows a line from the spectrometer 132 to the receiver and detection circuitry 120 to denote that the various excitation frequencies employed by the spectrometer are passed to the receiver and detection circuitry.

Thirdly, it is important to generate as uniform a $B_1$ field across the sample as possible, to avoid worsening any dephasing problem which may exist. In order to achieve this, it may be important to impose various restrictions on the design of the radio-frequency transmitting and receiving coil forming part of the r.f. probe 112 shown in FIG. 1. For example, the r.f. coil might preferably be a planar surface coil or a spiral coil, a solenoid, or a solenoid of variable pitch.

Fourthly, if the temperature inhomogeneity in the sample is very significant, it may be necessary to retune and/or rematch the radio-frequency transmitting and receiving coil forming part of the r.f. probe 112 shown in FIG. 1.

Fifthly and finally, it is important to apply digital bandpass filtering to the free-induction decay using a filter of bandwidth appropriate for the excitation bandwidth of each of the applied frequencies. The filter bandwidth may suitably be less than twice or 1.5 times the relevant excitation bandwidth. As explained later, this can enhance the sensitivity of detection.

An example of the operation of the present invention is now described. In the example, the 5192 kHz signal in RDX at 298 K is considered; for this transition, $T_1$=10 ms, $T_2$=8 ms, $T_2^*$=1.5 ms and the temperature coefficient of the frequency is –0.52 kHz $K^{-1}$. The $T_2^*$ value of 1.5 ms corresponds to a line-width at half-height of about 0.2 kHz for a Lorentian spectral shape. Suppose the temperature gradient across the sample is uniform and equal to 4° C. This corresponds to a range of resonance frequency of 2 kHz, say from a mean of 5192±0.5 kHz in one of two "regions" into which the sample is notionally divided to 5191±0.5 kHz in the other such region. At a centre excitation frequency of 5191.5 kHz, serious dephasing of both resonance response signals with respect to the carrier is likely to occur in a time of (say) 0.3 to 0.5 ms. A single rectangular phase, of excitation band width 2 kHz and length 0.3 ms, would give rise to a serious loss in sensitivity in the presence of such a temperature gradient, depending on the time after the end of the pulse at which acquisition begins.

According to one preferred embodiment of the present invention, rather than a single pulse being used, at least two rectangularly shaped frequency/phase swept such pulses are used. In the present example, one has a centre frequency of 5192.0 kHz and the other a centre frequency of 5191.0 kHz. Both have an excitation band width of 1 kHz. Hence both (centre) excitation frequencies fall within the range of the resonance frequency, and furthermore the pulses do not overlap each other. Hence use of such pulses can reduce dephasing effects due to the temperature inhomogeneity in the sample.

In the present example, for the same r.f. power as would be required for a single rectangular pulse, with two frequency/phase swept pulses the pulse length may be maintained at 0.3 ms despite the reduced bandwidth, or possibly even may be reduced below 0.3 ms. For frequency/phase swept pulses the length of the pulse is not necessarily related to the excitation bandwidth. Data acquisition should take place with the minimum delay. Significant dephasing with respect to the carrier now takes place in 0.6 to 1.0 ms, so that the loss in sensitivity is considerably reduced. It is to be noted that by using pulses of reduced bandwidth it may be possible to increase the flip angle of the pulses at the same r.f. power.

Alternatively, four such pulses, of frequencies 5190, 5191, 5192 and 5193 kHz, could accommodate a total temperature gradient of 8° C., or else an uncertainty in the mean temperature of 4° C. and a temperature gradient across the sample of 4° C. It is not necessary to lengthen unduly the total signal acquisition time by the use of these frequency stepped pulses. If $T_1$ is 10 ms, and only a single shaped pulse were being used, it would be usual to set the pulse repetition time to (say) 20 ms. Four or even eight frequency stepped shaped pulses could be inserted into this time interval, with adequate time to generate the pulse and leave sufficient time to acquire the free induction decay. Since these pulses excite only a particular region of the sample, the effective pulse repetition time is still 20 ms.

It is anticipated that some adjustment to the figures given in this example may in some circumstances be necessary to allow for the fact that the different regions of the sample will not only exhibit different resonance frequencies but will also have different spin-lattice relaxation times. Appropriate adjustment can be made according to the teachings of the aforementioned International Patent Publication No. WO 92/17794.

In the example, the signals generated in the frequency stepped sequences are separately processed in the receiver and detection circuitry. Each frequency response may then be separately examined, or the responses summed to provide a total response from the sample.

In general terms, supposing n stepped frequencies are used, in summing the n step responses, it would be expected that the overall signal-to-noise ratio would be reduced by a factor of √n relative to the case in which all such responses were to be simultaneously excited and detected, by means of a single pulse or pulse sequence sufficient to cover the entire excitation band width Δv. However, by application to each step response during signal processing of a narrow bandpass filter whose width is 1/n th of that which would be used if the total response were to be detected, that is, whose width is Δv/n, the signal-to-noise ratio of each step response is increased by a factor of √n. Hence the overall signal-to-noise ratio of the summed response can remain unchanged.

A pulse timing diagram showing the operation of the preferred embodiment of the present invention is now described with reference to FIG. 3. Two repeating series of radio frequency pulses at different frequencies are applied in staggered, interleaved fashion. The pulses of the two series are shaped so as to have a rectangular shape in the frequency domain, and are of width $t_w^{(1)}$ and $t_w^{(2)}$ and of differing frequencies $f_1$ and $f_2$. The two frequencies are assumed to be associated with different values of the spin-lattice relaxation time, $T_1$, on account of the different temperatures to which they correspond. The pulses are repeated at pulse repetition times $\tau$ ($\tau >> t_w$) which are much longer than the longer $T_1$—say $\tau$=5$T_1$—to ensure full signal recovery between pulses; phase shifts of alternate pulses or suitable combinations of pulses of width $t_w$ and 2$t_w$ may be used to eliminate probe ringing. After phase-sensitive detection and manipulation of the appropriate signals, the residual oscillations can be made to cancel and only the true NQR response signal is observed. Since $\tau$ is much longer than either $T_1$ value, in this particular case no $T_1$ compensation is necessary.

The overall time of the test is limited by the longer $T_1$; if $\tau$=5$T_1$ (where $T_1$ is the longer $T_1$ value) and the allowed observation time is $T_{obs}$, the maximum number of accumulations possible is N=$T_{obs}/(t_w+\tau)$=$T_{obs}/(t_w+5T_1)$. Signal/noise ratio is proportional to the square root of N, so that it is important to set the pulse repetition time $\tau$ so that $\tau$ is not significantly longer than 5$T_1$; otherwise information is lost.

A restriction on the separation, $\tau_f$, between the two pulses is that $\tau_f$ should exceed, say, $2T_2^*$ or $3T_2^*$, in order to allow the f.i.d. from the first pulse to decay substantially before the second pulse is applied. Since $T_2^*$ may vary, for example, with temperature, it may be important to adjust $\tau_f$ to compensate for this.

In an alternative form of the preferred embodiment, the pulse repetition time $\tau$ is made less than $5T_1$ (where $T_1$ is now the shorter $T_1$ value) and the pulse width and/or rf power adjusted to produce flip angles which are less than the flip angle corresponding to the maximum f.i.d and which allow for the variation of $\tau/T_1$ with temperature, as described in the international patent application referred to earlier. That is, the excitation is such as would produce equal signal strengths at the temperatures at which $f_1$ and $f_2$ are the resonant frequencies. The signals are weaker than when $\tau/T_1$ is approximately equal to 5, but more can be accumulated in a given time and a lower r.f. power is required.

Figure 3:
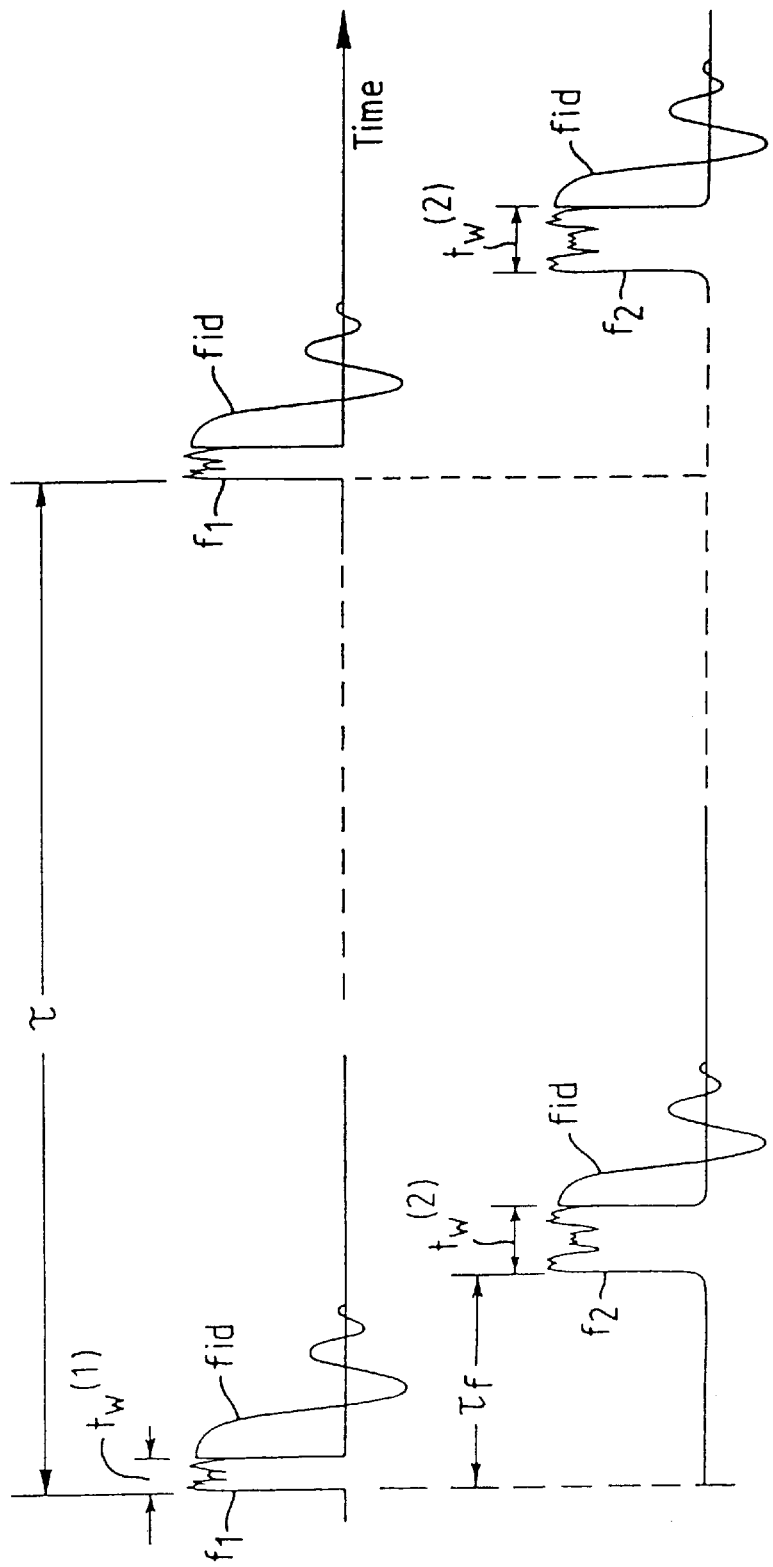
FIG. 3 is a pulse timing diagram for a preferred embodiment of the present invention.

Whilst the pulse timing diagram illustrated in FIG. 3 is suitable for the generation and detection of free induction decay signals, alternatively or additionally echoes may be generated or detected by suitable adjustment of the pulse repetition time $\tau$. These may be single echoes, or multiple echoes (generated using a multiple pulse sequence).

The use of echoes can to an extent re-focus the dephasing response signals, and therefore reduce the problems caused by inhomogeneities in the sample.

However, the re-focusing would not be expected to occur to a full extent due to the limited bandwidth over which multiple pulse sequences can function successfully. Multiple pulse sequences generally suffer from poor off-resonance performance.

For this reason, it is believed that the use of echoes can not by itself fully cure the inhomogeneity problems referred to previously. One of the other techniques described herein, such as the use of multiple frequencies or a particularly favourable resonance of the nuclear species of interest, would usually need to be employed additionally.

The use of echoes is also advantageous because it can generate extra information concerning the nuclear species of interest, through the measurement of both echo decay times and free-induction times.

In cases where the sample exhibits a multiplicity of resonance response signals, with different temperature coefficients, it has been found to be advantageous to select for detection that transition with the lowest value of temperature coefficient, provided that the relaxation times are not otherwise unfavourable. For example, taking the case of RDX again, there are in total nine known $^{14}$N quadrupole resonances, clustered in triplets around frequencies of 1.8, 3.4 and 5.2 MHz. Around 3.4 MHz, at room temperature the three resonances are at frequencies of 3.46, 3.41 and 3.36 MHz. Of the nine resonances, that at 3.41 MHz (298K) is exceptional, in that, it has now been discovered, it has a temperature coefficient of only −0.094 kHz K$^{-1}$, which is roughly one sixth of that of the 5.19 MHz resonance and indeed very considerably less than that of any of the other resonances.

In a further preferred embodiment, therefore, a single shaped or simple rectangular pulse or a series of such pulses at a single excitation frequency may then be sufficient to accommodate a temperature gradient of 12° C. across the sample, or a gradient of 6° C. and mean temperature uncertainty of not more than 6° C. $T_2^*$ for this particular transition is 0.7 ms (corresponding to a line width of 0.4 kHz) so that the shaped (or rectangular) pulse must have a length not appreciably larger than this value.

It is noted in passing that the spin-lattice relaxation time, $T_1$, of the 3.41 MHz line has a temperature coefficient similar to that of the 5.19 MHz line. Therefore compensation for the variation of $T_1$ with temperature may still need to be effected, as described above.

A similar analysis is now presented for the drug Cocaine, either in the form Cocaine Base or in the form Cocaine Hydrochloride. It has been found that the line at 3.82 MHz at room temperature, for Cocaine Base, or that at 0.961 MHz, for Cocaine Hydrochloride, is the least sensitive in terms of the dependence of resonance frequency on temperature.

In connection with the further preferred embodiment, in general terms, a disadvantage of choosing a line at lower frequency is a loss in signal-to-noise (SNR) ratio (SNR $\alpha$ $v_Q^{3/2}$). For RDX, choosing the 3.41 rather than the 5.19 MHz line for RDX would thus be expected to involve a halving of the signal-to-noise ratio.

However, it has now been found pursuant to the present invention that this loss can be partially or completely compensated in any or all of three ways illustrated with reference to the 3.41 and 5.19 MHz transitions of the explosive RDX.

Firstly, in cases where the product of $B_1$ and the excitation frequency needs to be maintained at or below a given level, the $B_1$ field can be increased in the ratio of the inverse of the frequencies (in the present example, in the ratio 5.2 to 3.4, i.e. 1.5). This can enable the flip angle to be increased, and hence the observed signal, to an extent which depends on the ratio $\tau/T_1$, where $\tau$ is the pulse separation. Assuming the flip angles increase in the same ratio as the $B_1$ field, signal-to-noise gain could be approximately 1.25.

Secondly, use of the 3.41 rather than the 5.19 MHz line of RDX could permit a reduction in excitation bandwidth by a factor of 6, from, say 20 to 3.5 kHz. A suitably modified shaped pulse or a rectangular pulse of much reduced width, say 170 $\mu$s, could be used for the same r.f. power, thus, for example, diminishing the time from the centre of the pulse to the beginning of signal acquisition.

This second feature has two other advantages; the shorter the time between pulse and signal acquisition, the less the effects of signal dephasing due to the temperature gradient; in addition, in the case of RDX, for example, it can overcome the otherwise deleterious effects of selecting a signal (3.41 MHz) with a shorter $T_2^*$ (0.7 ms) and broader line (0.4 kHz) than the 5.19 MHz line (1.4 ms, 0.2 kHz).

Thirdly, the selection of a narrower excitation bandwidth implies that a narrower bandpass filter can be used in signal processing. In the case of RDX, for example, the filter width can be reduced by a factor of six, from, say, 24 to 4 kHz. This could yield an improvement in SNR (other factors remaining the same) of $\sqrt{6}=2.45$.

A suitable bandpass filter would be a Blackman-sine filter (or "Blackman window" filter) as described in a paper entitled "Selective Detection in NMR by Time-Domain Digital Filtering" (M. E. Rosen, J. Magn. Reson., 1994, 107, 119).

All factors being taken into account, it is now believed that choosing a line at 3.41 rather than 5.19 MHz, for RDX, will only marginally reduce the sensitivity of the tests.

A further example of the operation of the present invention is now described with reference to FIGS. 4 to 7 of the drawings.

Figure 4:
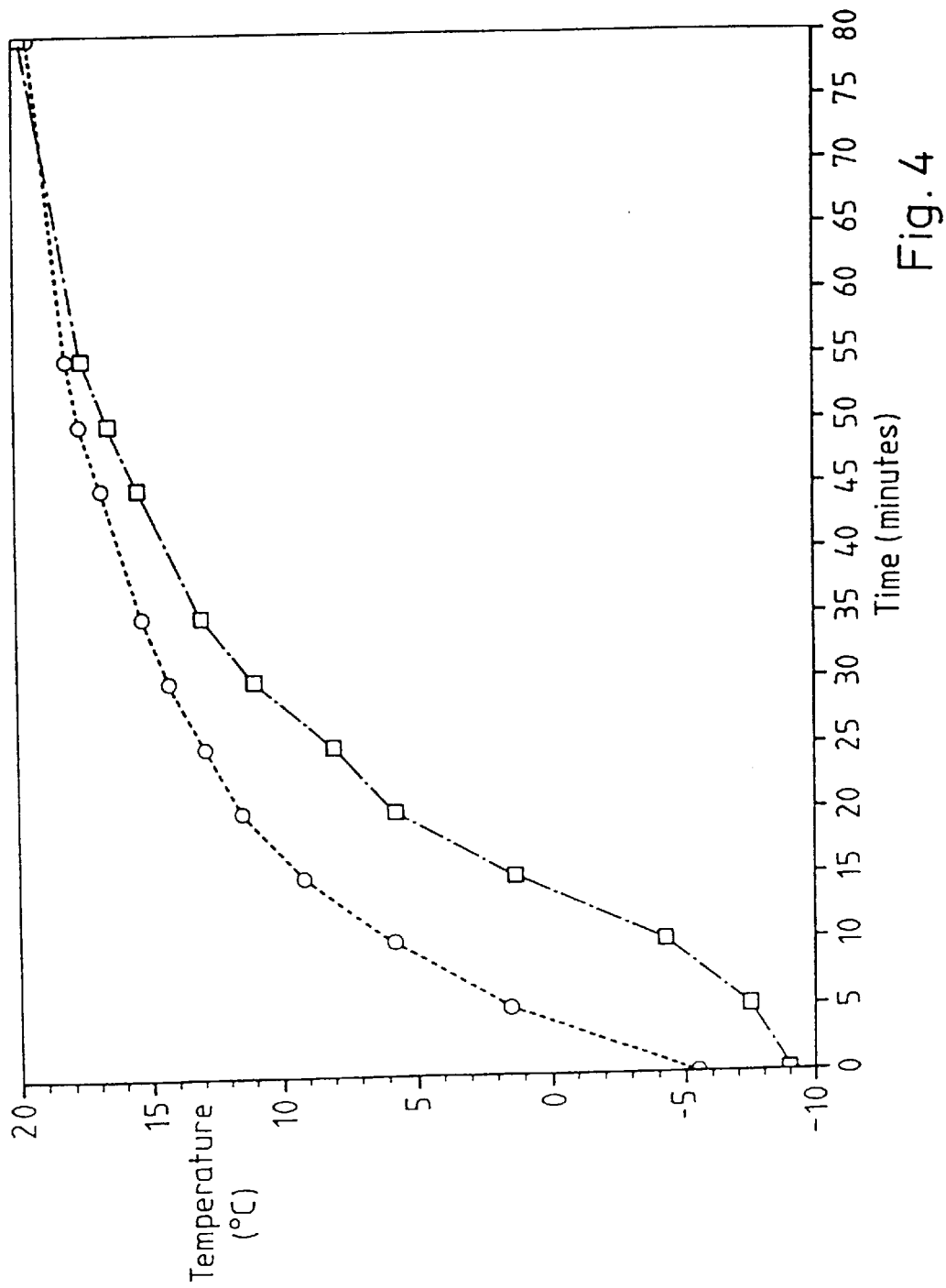
FIGS. 4 show the variation of temperature with time for a set of experiments.

In the example, results are provided of experiments conducted for the explosive RDX at nominal resonance frequencies of 5.19 MHz and 3.41 MHz. The explosive was in the form of a cylindrical sample, 5 cm in diameter and 6 cm long, and weighing approximately 200 g. A temperature differential was created in the sample first by lowering its temperature to about −9° C. in a freezer and then by returning it to the ambient (at approximately 22° C.). FIG. 4 shows the variation of temperature of the sample with time, the temperature measurements being taken with sensors one at the centre of the sample (see the square data points) and one near the cylindrical surface centre (see the circular data points). The results were obtained with the r.f. probe 112 in place but without the excitation pulses present. Assuming r.f. heating is small the results would be expected to give a reasonable indication of the temperature gradient in the sample during the measurements now to be described.

An examination of FIG. 4 reveals that the temperature differential in the sample lasts for at least an hour.

FIGS. 5 show the 5.19 MHZ line at a) t=0, b) t=2 mins, c) t=4 mins, d) t=6 mins and e) t=15 mins after the sample was placed in the r.f. probe 112. In FIGS. 5(a) to 5(d), each of the subdivisions on the horizontal frequency axis is separated by 2.5 kHz. In FIG. 5(e), the separation of the subdivisions is 12.5 kHz. The dotted line represents the single excitation frequency of 5206 kHz (5199 kHz for FIG. 5(e)). For the experiment, a simple rectangular pulse sequence was employed. The duration of each pulse was 150 $\mu$s.

Initially (FIG. 5(a)) a good signal is obtained. The resonance frequency suggests a temperature of roughly −7° C. However, the signal rapidly deteriorates under the conditions used so that by t=6 mins (FIG. 5(d)) only two broad weak features remain. At t=6 mins, the temperature differential between the centre and the end of the sample was in the region of 9° C. Finally, as the temperature differential in the sample eventually reduces, signal intensity again increases. At t=15 mins (FIG. 5(e)), a relatively strong signal is obtained, with two resonance lines. The larger one corresponds to a temperature of roughly 13° C. and the smaller one a temperature of roughly 3° C.

Figure 6:
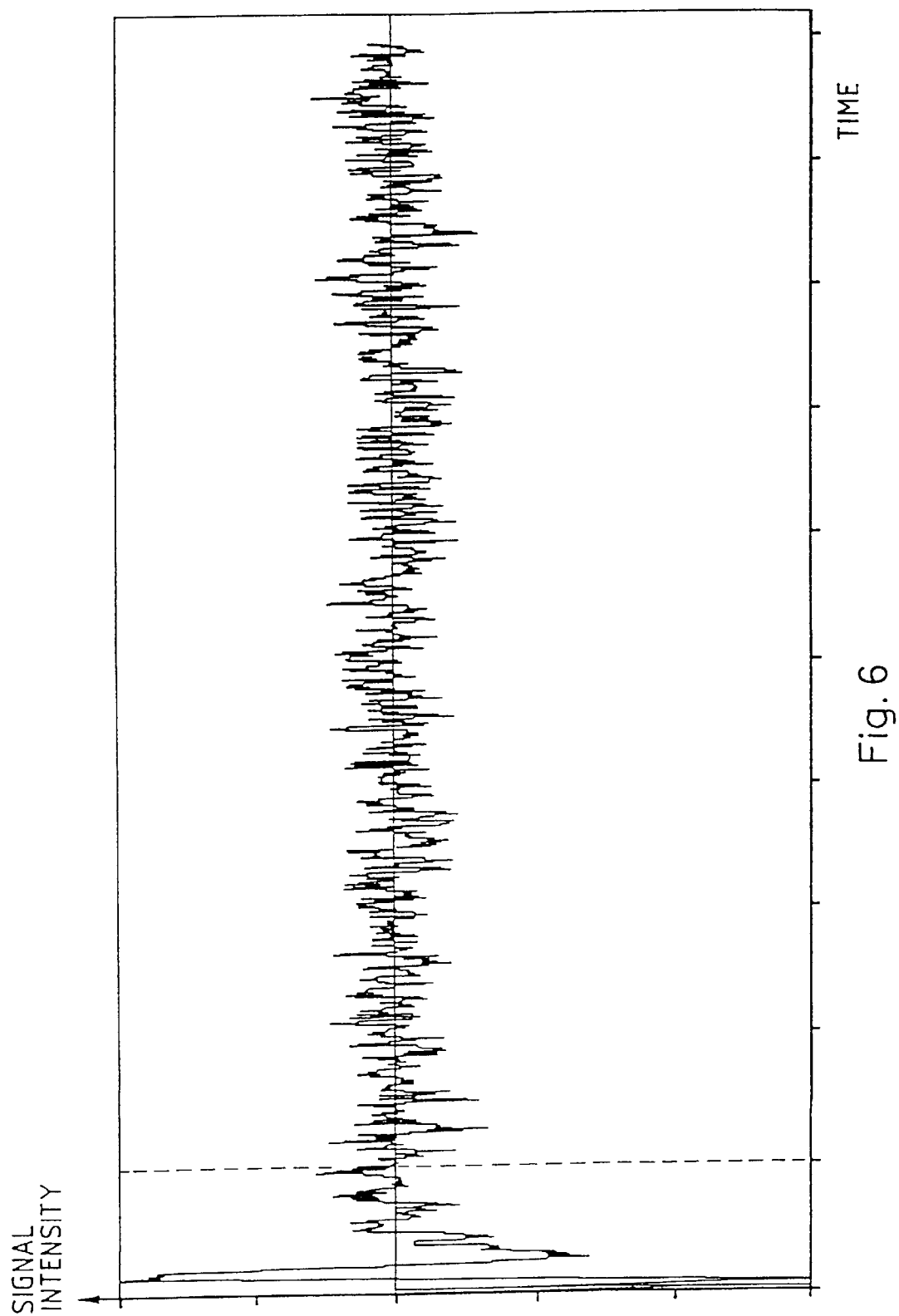
FIG. 6 shows the free induction decay corresponding to the fourth spectrum shown in FIGS. 5.

FIG. 6 shows the free induction decay resonance response signal corresponding to the spectrum of FIG. 5(d), that is, the signal after t=6 mins. Each subdivision on the horizontal axis represents 500 $\mu$s. As can be seen, there is still a strong signal in the first 50 $\mu$s, but this rapidly dephases to undetectable noise.

In other experiments, a somewhat stronger signal was obtained by using less data compression and by using a shorter sampling time. Hence in these other experiments a greater concentration of data points near the beginning of the response signal was employed. Also, zero filling from 100 $\mu$s was employed; zero filling is described in a book entitled "A Handbook of Nuclear Magnetic Resonance" (R. Freeman, Longman, 1987, pp.302–305). However the free induction decay was still comparatively weak.

It can be seen from the results of the experiment illustrated in FIGS. 5 and 6 that, in the presence of a marked temperature differential within a sample, and where no special measures are taken to counteract this, the resonance response signal may dephase to a level which is undetectable within a very short period.

Figure 7A:
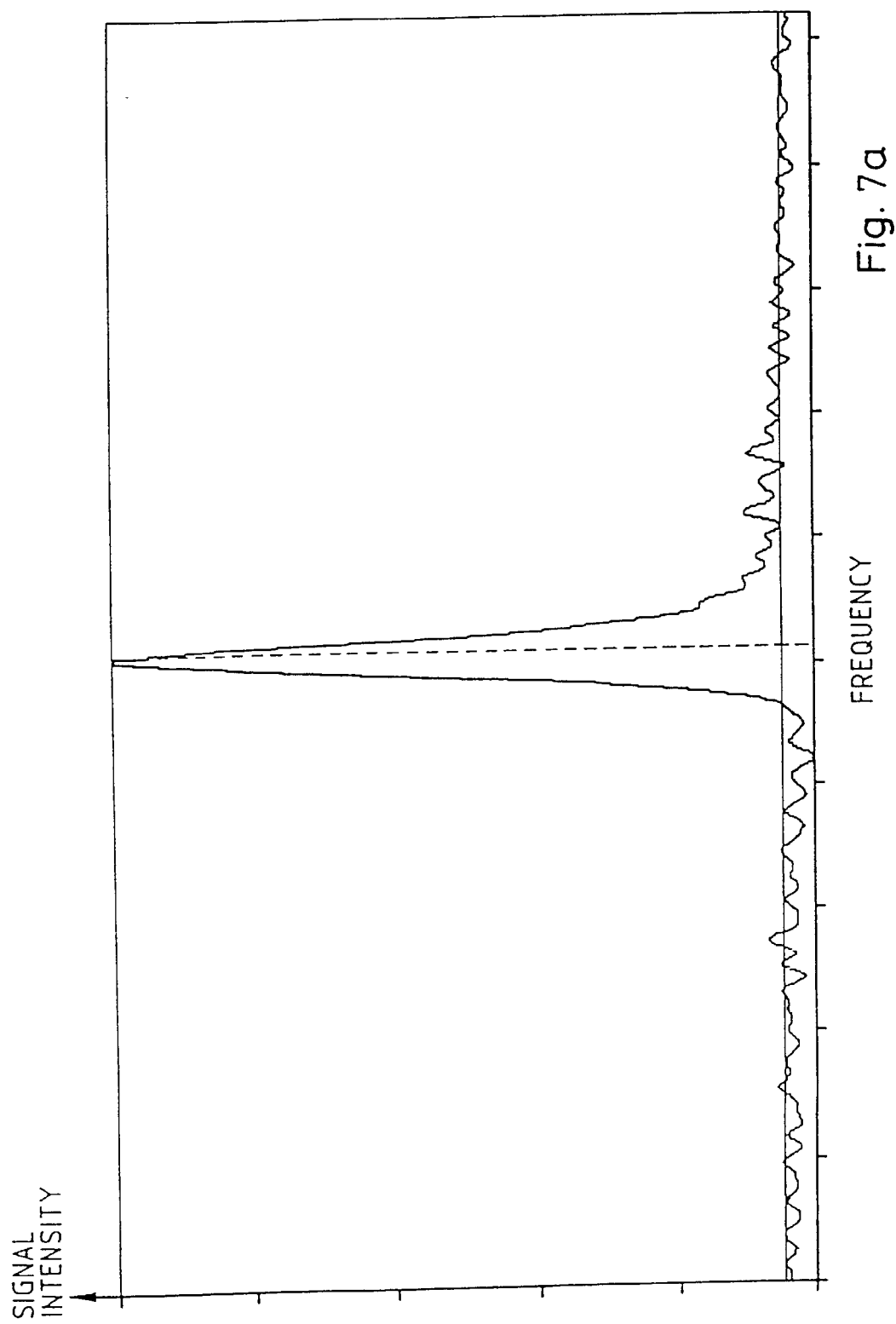
FIGS. 7 show spectra obtained at four different times during a second experiment.
Figure 7D:
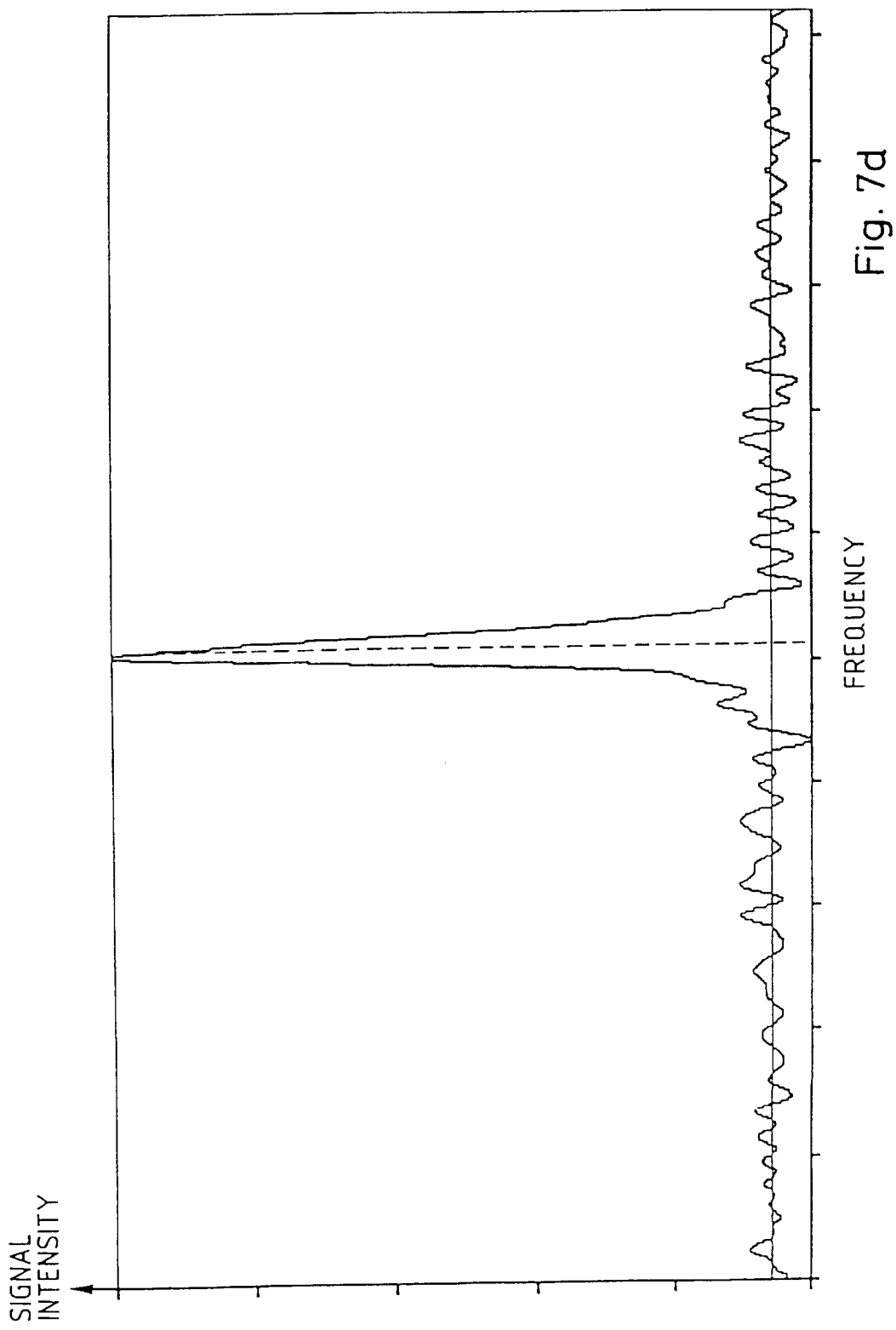

FIGS. 7 illustrate a further experiment in which special measures have been taken to counteract the temperature differential. In this case, these measures involve the use of the least temperature sensitive of the RDX lines, that at 3.41 MHz at room temperature. (This is the further preferred embodiment of the invention described above.) As with the previously described experiment, a simple rectangular pulse sequence was again employed, with the duration of each pulse equal to 150 $\mu$s. That is, the sequence was as described in relation to FIG. 3, but only at a single excitation frequency.

FIGS. 7 show the line at a) t=0, b) t=4 mins, c) t=6 mins and d) t=16 mins. Each of the subdivisions on the horizonal frequency axis is separated by 3.125 kHz. The dotted line represents the single excitation frequency of roughly 3412 kHz. While some change in line shape is seen at b) t=4 mins, there is much less change in the observed signal for this line, using rectangular pulses, than is seen for the 5.19 MHz line. By t =40 mins (not illustrated), the signal had almost fully recovered.

Hence it can be seen that in the present case use of the RDX line with the least temperature dependence can largely eliminate the problem of loss of signal associated with the differential temperature induced dephasing.

In a further experiment, which was similar to that described above (using the 3.41 MHz RDX line), a sequence of shaped pulses each of duration 250 $\mu$s was employed.

The dephasing effects encountered using the shaped pulses were somewhat worse than those encountered using the simple rectangular pulses. It is believed that the reason for this is the relative bandwidth of the pulses used. It should be possible to obtain better results using shaped pulses of reduced bandwidth.

Each feature disclosed in the description, and (where appropriate) the claims and drawings may be provided independently or in any appropriate combination.

It will of course be understood that the present invention has been described above purely by way of example, and modifications of detail can be made within the scope of the invention.

What is claimed is:

1. A method of detecting a presence of a sample containing a given species of quadrupolar nucleus, comprising:
   applying excitation to said sample to excite a quadrupole resonance of said given nuclear species for which a particular property has least sensitivity to a given extrinsic parameter; and
   detecting a resonance response signal.

2. A method according to claim 1 wherein said particular property is resonance frequency.

3. A method according to claim 1 wherein said sample is subjected to an inhomogeneous distribution of said extrinsic parameter.

4. A method according to claim 1 wherein said extrinsic parameter has an unknown value.

5. A method according to claim 1 wherein said sample comprises a substance which has a plurality of distinct resonance frequencies, and said resonance which is excited does not have the highest resonance frequency.

6. A method according to claim 1 wherein said sample comprises a substance which has a plurality of sets of resonance frequencies, and said resonance which is excited does not have a resonance frequency in the highest set of resonance frequencies.

7. A method according to claim 1 wherein said sample comprises RDX.

8. A method according to claim 7 wherein a resonance at 3.41 MHz, at 298 K, is excited.

9. A method according to claim 1 wherein said excitation is arranged to generate an echo resonance response signal.

10. A method according to claim 1 wherein said sample is subjected to an inhomogeneous distribution of an extrinsic parameter and excitation is applied to said sample at a plurality of different excitation frequencies, such frequencies falling within a resonance frequency range for said nucleus corresponding to a range of said extrinsic parameter.

11. A method according to claim 10 wherein said excitation comprises pulses at said plurality of different excitation frequencies which are arranged to have respective excitation frequency ranges which are substantially non-overlapping.

12. A method according to claim 10 wherein said excitation comprises pulses at said plurality of different excitation frequencies, said pulses being shaped so as to have a substantially rectangular frequency profile.

13. A method according to claim 10 wherein a frequency separation between adjacent excitation frequencies is less than 0.1% of one such excitation frequency.

14. A method according to claim 10 wherein a frequency separation between adjacent excitation frequencies is less than 5 kHz.

15. A method according to claim 10 wherein a number of said plurality of different excitation frequencies is greater than 2.

16. A method according to claim 10 wherein said excitation is applied at adjacent excitation frequencies at different times.

17. A method according to claim 10 wherein a respective resonance response signal corresponding to each excitation frequency is detected at that excitation frequency.

18. A method according to claim 1 wherein said excitation is pulsed excitation comprising at least one pulse and a duration of said at least one pulse is less than twice a free induction decay time, $T_2^*$, appropriate to said quadrupole resonance.

19. A method according to claim 18 wherein said duration of said at least one pulse is less than $T_2^*$.

20. A method according to claim 1 wherein said excitation is pulsed excitation comprising at least one pulse and a duration of said at least one pulse is less than 5 ms.

21. A method according to claim 3 wherein a range of said extrinsic parameter is less than 100% of its mean absolute value.

22. A method according to claim 3 wherein a range of said extrinsic parameter is greater than 10% of its mean absolute value.

23. A method according to claim 3 wherein said extrinsic parameter is temperature and a range of temperature is less than 10 C.

24. A method according to claim 1 wherein said excitation has a time domain waveform and said excitation is applied to said sample over a given frequency range, said time domain waveform being phase modulated.

25. A method according to claim 1 wherein said excitation has a time domain waveform and said excitation is applied to said sample over a given frequency range, said time domain waveform being amplitude modulated.

26. A method according to claim 1 wherein said excitation has a time domain waveform and said excitation is applied to said sample over a given frequency range, said time domain waveform being both phase modulated and amplitude modulated.

27. A method according to claim 1 wherein said excitation is pulsed excitation covering a given frequency range, and said excitation is applied to said sample in such a way that a phase of said excitation varies generally non-linearly with an excitation frequency over said given frequency range.

28. A method according to claim 27 wherein said phase varies generally quadratically with a frequency off-set.

29. A method according to claim 1 wherein said extrinsic parameter one of temperature and pressure.

30. A method according to claim 1 wherein only that resonance of said given nuclear species for which said particular property has said least sensitivity to said given extrinsic parameter is excited.

31. A method according to claim 1 further comprising producing an alarm signal in dependence on whether said presence of said sample is detected.

32. A method of Nuclear Quadrupole Resonance testing a substance containing a given species of quadrupolar nucleus, the method comprising:
   applying excitation to said substance to excite a quadrupole resonance of said given species, said given species having a property that is least sensitive to a given extrinsic parameter; and
   detecting a resonance response signal, the resonance response signal being responsive to the applied excitation;
   wherein said substance comprises RDX; and
   wherein said resonance occurs at a frequency of 3.41 MHz and a temperature of 298 degrees Kelvin.

33. A method of detecting a presence of a substance containing a given species of quadrupolar nucleus, comprising:
   applying excitation to said substance to excite a quadrupole resonance of said given species, said given species having a property that is least sensitive to a given extrinsic parameter;
   detecting a resonance response signal, the resonance response signal being responsive to the applied excitation; and
   producing an alarm signal in dependence on whether said substance is detected;
   wherein said substance comprises RDX; and
   wherein said resonance occurs at a frequency of 3.41 MHz and a temperature of 298 degrees Kelvin.

34. A method of Nuclear Quadrupole Resonance testing a sample containing a given species of quadrupolar nucleus, comprising:
   applying excitation to said sample to excite a quadrupole resonance of said given nuclear species for which a particular property has least sensitivity to a given extrinsic parameter; and
   detecting a resonance response signal;
   wherein said sample is subjected to an inhomogeneous distribution of said extrinsic parameter.

35. A method of Nuclear Quadrupole Resonance testing a sample containing a given species of quadrupolar nucleus, comprising:
   applying excitation to said sample to excite a quadrupole resonance of said given nuclear species for which a particular property has least sensitivity to a given extrinsic parameter; and
   detecting a resonance response signal;
   wherein said sample comprises a substance which has a plurality of distinct resonance frequencies, and said resonance which is excited does not have the highest resonance frequency.

36. A method of Nuclear Quadrupole Resonance testing a sample containing a given species of quadrupolar nucleus, comprising:
   applying excitation to said sample to excite a quadrupole resonance of said given nuclear species for which a particular property has least sensitivity to a given extrinsic parameter; and
   detecting a resonance response signal;
   wherein said sample comprises a substance which has a plurality of sets of resonance frequencies, and said resonance which is excited does not have a resonance frequency in the highest set of resonance frequencies.

37. An apparatus for detecting a presence of a substance containing a given species of quadrupolar nucleus, comprising:

means for applying excitation to said substance to excite a quadrupole resonance of said given species, said given species having a property that is least sensitive to a given extrinsic parameter;

means for detecting a resonance response signal, the resonance response signal being responsive to the applied excitation; and means for producing an alarm signal in dependence on whether said substance is detected;

wherein said resonance occurs at a frequency of 3.41 MHz and a temperature of 298 degrees Kelvin.

38. An apparatus for detecting a presence of a substance containing a given species of quadrupolar nucleus, comprising:

a radio frequency probe for applying excitation to said substance and for detecting a resonance response signal; and a control computer adapted to control said radio frequency probe;

wherein said control computer and said radio frequency probe are adapted to apply excitation to excite a quadrupole resonance of said given species, said given species having a property that is least sensitive to a given extrinsic parameter;

wherein said resonance occurs at 3.41 MHz and at a temperature of 298 degrees Kelvin; and wherein said control computer is adapted to produce an alarm signal in dependence on whether said substance is detected.

* * * * *

UNITED STATES PATENT AND TRADEMARK OFFICE
CERTIFICATE OF CORRECTION

| | | |
|---|---|---|
| PATENT NO. | : 6,222,364 B1 | Page 1 of 1 |
| DATED | : April 24, 2001 | |
| INVENTOR(S) | : Smith et al. | |

It is certified that error appears in the above-identified patent and that said Letters Patent is hereby corrected as shown below:

<u>Title page,</u>
Item [62], Related U.S. Application Data: after "Jan. 27, 1997," please insert -- which was a continuation of international application No. PCT/GB95/02318, filed Sept. 29, 1995, --

<u>Column 1,</u>
Line 7, after "6,091,240" please insert --, which was a continuation of international application PCT/GB95/02318, filed Sept. 29, 1995 --

Signed and Sealed this

Eighteenth Day of December, 2001

Attest:

Attesting Officer

JAMES E. ROGAN
*Director of the United States Patent and Trademark Office*